United States Patent
Yamane et al.

(10) Patent No.: US 9,523,119 B2
(45) Date of Patent: Dec. 20, 2016

(54) METHOD OF DISTINGUISHING GENOTYPES

(75) Inventors: Akio Yamane, Kisarazu (JP); Mashimo Nakayama, Kisarazu (JP); Shiro Kitano, Kisarazu (JP)

(73) Assignee: TOPPAN PRINTING CO., LTD., Tokyo (JP)

( * ) Notice: Subject to any disclaimer, the term of this patent is extended or adjusted under 35 U.S.C. 154(b) by 98 days.

(21) Appl. No.: 13/248,321

(22) Filed: Sep. 29, 2011

(65) Prior Publication Data

US 2012/0077193 A1   Mar. 29, 2012

Related U.S. Application Data

(63) Continuation of application No. PCT/JP2010/002200, filed on Mar. 26, 2010.

(30) Foreign Application Priority Data

Mar. 31, 2009 (JP) ............... P2009-084967

(51) Int. Cl.
*C12Q 1/68* (2006.01)
*G01N 21/64* (2006.01)

(52) U.S. Cl.
CPC ............. *C12Q 1/686* (2013.01); *C12Q 1/6858* (2013.01); *G01N 2021/6441* (2013.01)

(58) Field of Classification Search
None
See application file for complete search history.

(56) References Cited

U.S. PATENT DOCUMENTS

| | | | |
|---|---|---|---|
| 5,688,643 A | 11/1997 | Oka et al. | |
| 5,948,618 A | 9/1999 | Oka et al. | |
| 6,355,431 B1 * | 3/2002 | Chee et al. | 435/6.11 |
| 2002/0001844 A1 * | 1/2002 | Frutos et al. | 436/6 |
| 2005/0239103 A1 * | 10/2005 | Brandt et al. | 435/6 |
| 2010/0129796 A1 * | 5/2010 | Halpern et al. | 435/6 |

FOREIGN PATENT DOCUMENTS

| | | |
|---|---|---|
| JP | 59-93099 | 5/1984 |
| JP | 59-148798 | 8/1984 |
| JP | 59-204200 | 11/1984 |
| JP | 1-252300 | 10/1989 |
| JP | 1-314965 | 12/1989 |
| JP | 2982304 | 9/1999 |
| JP | 2003-174882 | 6/2003 |
| WO | 95/02068 | 1/1995 |
| WO | 01/12849 A1 | 2/2001 |

OTHER PUBLICATIONS

Machine Translation of JP2003174882. 19 pages. Obtained on Sep. 25, 2012 using the IPDL tool.*
Morrison et al. Analytical Biochemistry (1989) 183: 231-244.*
Grow et al. Journal of Forensic Sciences (1996) 41(3): 497-502.*
Minora Tada et al., "Quantity of mutant K-ras gene in pancreatic secretions for diagnosis of pancreatic carcinoma with different assays: analysis of 100 patients", Clinica Chimica Acta 324, 2002, pp. 105-111.
K J Livak et al., "Oligonucleotides with fluorescent dyes at opposite ends provide a quenched probe system useful for detecting PCR product and nucleic acid hybridization", Genome Research, 1995, pp. 357-362.
Sanjay Tyagi et al., "Multicolor molecular beacons for allele discrimination", Nature Biotechnology vol. 16, Jan. 1998, pp. 49-53.
Larry E. Morrison, "Detection of Energy Transfer and Fluorescence Quenching", Nonisotopic DNA Probe Techniques, 1992, pp. 312-352.
Steven G. Daniel et al., "FastTag™ Nucleic Acid Labeling Systems: A Versatile Method for Incorporating Haptens, Fluorochromes and Affinity Ligands into DNA, RNA and Oligonucleotides", BioTechniques, vol. 24 No. 3, Mar. 1998, pp. 484-489.
James M. Prober et al., "A System for Rapid DNA Sequencing with Fluorescent Chain-Terminating Dideoxynucletoides", Science vol. 238, Oct. 1987, pp. 336-341.
Kevin M. Sullivan et al., "Automated DNA Profiling by Fluorescent Labeling of PCR Products", PCR Methods and Applications, 1992, pp. 34-40.
Gi Y. Jang et al., "Ligation mediated fluorescent labeling of DNA sequencing primers", Nucleic Acids Research, vol. 25 No. 4, 1997, pp. 922-923.
Gabor L Igloi et al., "Enzymatic Addition of Fluorescein- or Biotin-RiboUTP to Oligonucleotides Results in Primers Suitable for DNA Sequencing and PCR", BioTechniques, vol. 15, No. 3, 1993.
N.D. Sinha et al., "The preparation and applications of functionalised synthetic oligonucleotides: III. Use of H-phosphonate derivatives of protected amino-hexanol and mercapto-propanol or —hexanol", Nucleic Acids Research, vol. 16 No. 6, 1988, pp. 2659-2669.
Charles R. Petrie et al., "An Improved CPG Support for the Synthesis of 3'-Amine-Tailed Oligonucleotides", Bioconjugate Chem Technical Notes, 1992, pp. 85-87.
Takanori Oka et al., "A simple method for detecting single base substitutions and its application to HLA-DPB1 typing", Nucleic Acids Research, vol. 22, No. 9, 1994, pp. 1541-1547.

(Continued)

*Primary Examiner* — Angela M Bertagna

(57) ABSTRACT

The present invention relates to a method of distinguishing genotypes using PCR-PHFA including: a nucleic acid amplification step in which a mutation site-including region of a gene is amplified by a nucleic acid amplification reaction, thereby obtaining an amplification reaction solution; and a distinction step in which the amplification reaction solution obtained from the nucleic acid amplification step is mixed with a reference double-stranded nucleic acid having a specific genotype on the mutation site as well as being labeled with a labeling substance, and the mixture is subjected to a competitive strand displacement reaction, and the level of the occurrence of strand displacement is assessed so as to distinguish the identity; and the competitive strand displacement reaction is performed under a condition to suppress a polymerase extension reaction, and a genotype distinguishing kit for use in the distinct of genotypes by this method.

3 Claims, 6 Drawing Sheets

(56) References Cited

OTHER PUBLICATIONS

International Search Report mailed May 18, 2010 in corresponding International Patent Application No. PCT/JP2010/002200.
Shiro Kitano et al., "Detection of DNA mutations by fluorescence resonance energy transfer-based preferential homoduplex formation assay", Analytical Biochemistry, vol. 408, 2011, pp. 197-205.

Extended European Search Report dated Aug. 13, 2012 issued in corresponding European Patent Application No. 10758232.2.
International Search Report for PCT/JP2010/002200, mailed May 18, 2010.

\* cited by examiner

METHOD OF DISTINGUISHING GENOTYPES

CROSS REFERENCE TO RELATED APPLICATIONS

This application is a continuation application, filed under 35 U.S.C. §111(a), of International Application PCT/JP2010/002200, filed Mar. 26, 2010, which claimed priority to Japanese Application No. 2009/084967, filed on Mar. 31, 2009, the disclosures of which are hereby incorporated by reference.

TECHNICAL FIELD

The present invention relates to a method for distinguishing genotypes of gene polymorphisms, somatic mutations, and the like, and a kit for use in this method. More specifically, the present invention relates to a method to improve the discrimination accuracy in the method for distinguishing a very small difference between nucleotide sequences of nucleic acids through competitive hybridization that utilizes a strand displacement reaction, and a kit for use in this method.

Priority is claimed on Japanese Patent Application No. 2009-084967, filed Mar. 31, 2009, the content of which is incorporated herein by reference.

BACKGROUND ART

Thanks to the International HapMap Project which decodes the human genome, and especially makes SNP (Single Nucleotide Polymorphism) maps, information on the human genome is increasing more and more. In addition, research is progressing in a wide scale all over the world to find out the association between the thus acquired genomic information and individual constitutions, to understand genetic level variations between individual constitutions, and to realize "medication customized to the genetic information of each individual (personalized medicine)" which enables the diagnosis/treatment/prevention of diseases and the administration of drugs customized to individual traits. The genetic variations referred to herein mean variations in the nucleotide sequence of the genome between individuals, the most common type of variation of which is single nucleotide polymorphism (SNP). Moreover, in these days, it has been understood that variations in the number of repetitions (number of copies) of a short nucleotide sequence (Copy Number Variation: CNV) are widely spread in the whole genome, and also the associations between such CNV variations and diseases have been pointed out.

Here, in order to understand the genetic level variations between individuals, it is necessary to examine the genotypes of respective individuals. For example, a case is assumed in which it has been known that there are three genotypes of AA, AG, and GG in a certain type of SNP, wherein the symbol A represents an adenine base and the symbol G represents a guanine base. This SNP is an example consisting of cases where adenine or guanine comes to a specific position of a given genome. Accordingly, the test for distinguishing genotypes of this SNP is to determine the genotypes of these three variations. In other words, this discrimination can be achieved by seeing whether A accounts for 0 or 100, whether G accounts for 0 or 100, or whether A and G respectively account for 50 and 50. In this way, the detection of germline mutations such as SNP can be said to be substantially qualitative. Various kinds of relatively easy and convenient methods thereof have been adopted in practice.

On the other hand, when it comes to cancer cells, the onset is considered to be such that a somatic level mutation takes place and abnormal growth is triggered by this mutation. Accordingly, some specific kinds of cancer cells show mutations in specific genes. Thus, it is possible to detect such cancer cells by seeing the indication of this kind of mutation. However, cancer cells are so various that it is not always easy to specify cancer cells only by seeing a single kind of mutation.

Moreover, in recent pharmaceutical treatments, medicines which target specific types of molecules (such as a protein) in vivo have been developed, and some of which that can provide high efficacy with small side effects are being discovered. These are called molecularly targeted agents, and are actively developed mainly in the field of cancer treatment. Quite recently, it has been revealed to be impossible for these molecularly targeted agents to exert the efficacy of such medicines in the case where a mutation takes place in a protein on the downstream of the signal transduction of the targeted molecule. In this case, it is becoming possible to predict the efficacy of the medicine by examining a mutation in a gene which encodes the protein where the mutation takes place. A new field of personalized medicine which is different from the SNP detection is being opened.

Most of above-mentioned mutations specific to cancer cells or mutations showing the resistance to molecularly targeted agents are somatic mutations. In a case of the germline mutation mentioned above, every cell shows a common mutation; whereas, in a somatic mutation, only mutated cells show a mutation and non-mutated cells (usually, normal cells) shows no mutation. Accordingly, the situation is usually such that mutated cells and normal cells are mixedly present in the analyte (the specimen serving as the subject to be tested), and the mutant gene and the normal genes are both present in proportion to the abundance ratio of these cells. That is to say, in a case where normal cells account for the majority of the specimen and mutated cells account for only a part of it, it is necessary to detect the mutant gene which is scantily present within a large population of the normal gene. This differs from the detection of a germline mutation, and makes it more difficult to detect a somatic gene mutation.

The approach for detecting a somatic gene mutation is largely classified into two methods. One is a method to discriminate the normal gene and the mutant gene at a stage of the gene amplification. Concretely, this is a method to specifically amplify only the mutant gene.

For example, the method deemed to be most sensitive is a so-called "mutant-enriched PCR" method in which only the normal gene is cleaved using a restriction enzyme and only the non-cleaved mutant gene is amplified (for example, refer to Non-patent Document 1). This method is said to be capable of detecting the mutant gene at a concentration of one molecule per $10^6$ normal gene molecules through repetition of reactions to amplify the mutant gene (for example, refer to Non-patent Document 2). This method is excellent in terms of high sensitivity in this way. However, it is not a method applicable to general diagnoses because the manipulation is quite complicated.

In addition, a method has been developed in which, in PCR or such a primer extension reaction, the amplification is performed after discriminating a single nucleotide difference. This method is called "ARMS (amplification refractory mutation system)" (for example, refer to Non-patent Document 3), "ASPCR (allele specific PCR)" (for example, refer to Non-patent Document 4), or the like. This method is excellent as it is relatively highly sensitive, requires no manipulation other than usual PCR amplification reactions, is capable of carrying out all the reactions in a closed system, is very easy and convenient, and is free from PCR carry-over contamination. However, this can also be said to be a method involving a high risk of quasi-positive, because, even once a normal gene has been accidentally amplified by misdistinguishing a single nucleotide, the normal gene would be amplified in the following amplification reactions afterwards likewise of the mutant gene amplification. When adopting this method, it is necessary to strictly control the reaction conditions, namely, the reaction temperature, the salt concentration, and the like, and it is also necessary to strictly control the amount of the template (for example, refer to Non-patent Document 5). So, this method is not suitable for clinical tests where a large number of unspecified analytes have to be examined, nor diagnosis methods that should be easy and convenient as well as being highly accurate.

An other approach for detecting a somatic gene mutation is a method in which the mutant gene and the normal gene are concurrently amplified, and thereafter the mutant gene and the normal gene are discriminated and detected. The method for discriminating and detecting the thus amplified mutant gene and normal gene can be exemplified by various kinds of methods using electrophoresis, methods using hybridization, and the like (for example, refer to Non-patent Document 5). However, in most of these methods, it is difficult to accurately detect a small population of mutant gene contained in a large population of normal gene. For example, the method deemed to be the gold standard for detecting a mutant gene is a dideoxy sequencing method. The dideoxy sequencing method is capable of detecting a mutant gene with a relatively high sensitivity. Nonetheless, in cases where the mutant gene and the normal gene are mixedly present, the detection sensitivity for the mutant gene is about 10%, meaning that detection with a very high sensitivity is not feasible. Besides, it is reported that a pyrosequencing method is capable of increasing the detection sensitivity up to about 5%, and is superior to the dideoxy sequencing method (for example, refer to Non-patent Document 6).

Also developed is a method in which a mutation-including sequence is amplified by PCR, then the melting curve of the double-stranded DNA of the amplicon is obtained, and the ratio of the mutant gene is calculated from the difference in the melting curve between the mutant gene and the normal gene. This method is also considered to be capable of detecting a mutant gene contained in a mass of the normal gene with a sensitivity up to about 5% (for example, refer to Non-patent Document 7).

In addition, a PCR-PHFA method which utilizes a strand exchange reaction between two strands having homologous nucleotide sequences (strand displacement reaction) has been developed. The PCR-PHFA method is a method to detect a mutation by utilizing the following phenomenon such that: if the nucleotide sequences of a sample whose genotype is to be distinguished (double-stranded nucleic acid) and a reference double-stranded nucleic acid whose sequence is already known are completely identical, respective strands can not be discriminated and a strand exchange (strand displacement) takes place therebetween; whereas, if these are not identical even only by a single nucleotide difference, strands having completely homologous nucleotide sequences are preferentially paired to form a duplex, and therefore the exchange would not take place between the sample and the reference double-stranded nucleic acid. By using this PCR-PHFA method, it is reportedly possible to detect a mutant gene in the actual analyte with a high sensitivity of about 1% (for example, refer to Non-patent Document 8). In this way, the PCR-PHFA method is a highly reproducible method with a high detection sensitivity. However, the manipulation is a little complicated (for example, refer to Patent Document 1) and also involves carry-over contamination and such problems. In order to solve these problems, several types of improved methods have been proposed.

For example, Patent Document 2 discloses a method as an improved PCR-PHFA method which utilizes fluorescence resonance energy transfer. In PCR-PHFA methods for accurately measuring a very small population of mutant gene with a high sensitivity, it is necessary to detect a strand exchange between two double-stranded nucleic acids having homologous nucleotide sequences, in many cases of which, however, the sample double-stranded nucleic acid is not labeled, while the reference nucleic acid whose sequence is already known to be subjected to the strand exchange is labeled. In the method of Patent Document 2, a vicinity of the 5' end of one strand of the reference nucleic acid is labeled by binding a fluorescent substance, and a vicinity of the 3' end of the other strand is labeled with a different fluorescent substance. If no strand displacement reaction takes place and the reference nucleic acid remains as the initial duplex, a fluorescence resonance energy transfer between two different fluorescent substances is observed. In contrast, if a strand displacement reaction with the sample double-stranded nucleic acid takes place, no fluorescence resonance energy transfer is observed. Accordingly, the level of strand exchange can be assessed by measuring the level of this fluorescence resonance energy transfer.

Meanwhile, recent gene detection technologies are remarkably progressing, and methods for simultaneously detecting expressions or mutations of a large number of genes have been developed as an ensemble of a minute processing technique and a fluorescence detection method. Highly sensitive detection for a mutant gene that can be combined with these technologies has been desired. Furthermore, by conducting PCR-PHFA in a reaction vessel as a closed system rather than in a tube, the risk of contamination can be drastically reduced, and application to easy, convenient, and quick nucleic acid tests is possible.

REFERENCES

Patent Documents

Patent Document 1: Japanese Patent (Granted) Publication No. 2982304
Patent Document 2: Japanese Laid-Open Patent Application No. 2003-174882

Non-Patent Documents

Non-patent Document 1: Chen and another, Analytical biochemistry, 1991, Vol. 95, pp. 51 to 56.
Non-patent Document 2: Jacobson and another, Oncogene, 1994, Vol. 9, pp. 553 to 563
Non-patent Document 3: Newton and seven others, Nucleic acids research, 1989, Vol. 17, pp. 2503 to 2516

Non-patent Document 4: Wu and three others, Proceedings of the National Academy of Sciences of the United States of America, 1989, Vol. 86, pp. 2757 to 2760

Non-patent Document 5: Nollau and another, Clinical Chemistry, 1997, Vol. 43, pp. 1114 to 1128

Non-patent Document 6: Ogino and nine others, The Journal of Molecular Diagnostics, 2005, Vol. 7, pp. 413 to 421

Non-patent Document 7: Krypuy and four others, BMC Cancer, 2006, Vol. 6, p. 295

Non-patent Document 8: Tada and seven others, Clinica Chimica Acta, 2002, Vol. 324, p. 105

DISCLOSURE OF INVENTION

Problems to be Solved by the Invention

Conventional types of PCR-PHFA methods are not sufficient in sensitivity to discriminate nucleotide sequences through a strand displacement reaction, and it has been difficult for these methods to accurately detect/distinguish gene mutations, in particular, somatic mutations. For example, the PCR-PHFA method which utilizes fluorescence resonance energy transfer of Patent Document 2 is easy and convenient because it does not require complicated manipulation for solid-liquid separation. This method is excellent since the risk of contamination is drastically reduced by conducting PCR-PHFA in a reaction vessel as a closed system. However, the discrimination sensitivity is not yet sufficient.

Under such situations, it is an object of the present invention to provide: a method capable of improving the accuracy to discriminate a difference between nucleotide sequences, in the method for distinguishing genotypes that utilizes PCR-PHFA; and a kit suitable for this method.

Means to Solve the Problems

In general, the PCR-PHFA method often uses a sample double-stranded nucleic acid that has been prepared by a polymerase chain reaction (PCR). Conventionally, in order to facilitate the manipulation, the PCR reaction solution is not purified but directly mixed with the reference nucleic acid whose sequence is already known to be subjected to the strand exchange, and the mixture is supplied to the competitive strand displacement reaction.

The inventors of the present invention have conducted earnest studies so as to solve the above-mentioned problems. As a result, they have discovered that, upon the discrimination of genotypes by using a PCR-PHFA method, the sensitivity to discriminate genotypes can be improved by inhibiting the polymerase extension reaction in the competitive strand displacement reaction in cases where the nucleic acid amplification reaction solution is not purified but directly added to the reaction solution for the competitive strand displacement reaction. This has led to the completion of the present invention.

That is, the present invention includes the following items (1) to (10).

(1) A method of distinguishing genotypes of a gene mutation including: a nucleic acid amplification step in which a mutation site-including region of a gene contained in a specimen is amplified by a nucleic acid amplification reaction, thereby obtaining an amplification reaction solution which includes a specimen double-stranded nucleic acid; and a distinction step in which the amplification reaction solution obtained from the nucleic acid amplification step is mixed with a reference double-stranded nucleic acid having a specific genotype on the mutation site as well as being labeled with a labeling substance, and the mixture is subjected to a competitive strand displacement reaction, and a level of an occurrence of strand displacement between the reference double-stranded nucleic acid and the specimen double-stranded nucleic acid is assessed so as to distinguish an identity between the reference double-stranded nucleic acid and the specimen double-stranded nucleic acid, wherein the competitive strand displacement reaction is performed under a condition to suppress a polymerase extension reaction.

(2) The method of distinguishing genotypes according to the above-mentioned item (1), wherein the competitive strand displacement reaction is performed under the presence of an extension reaction inhibitor.

(3) The method of distinguishing genotypes according to the above-mentioned item (2), wherein the extension reaction inhibitor is a chelating agent.

(4) The method of distinguishing genotypes according to the above-mentioned item (3), wherein the extension reaction inhibitor is EDTA, and the EDTA concentration in a reaction solution of the competitive strand displacement reaction is 15 mM or higher.

(5) The method of distinguishing genotypes according to the above-mentioned item (2), wherein the extension reaction inhibitor is a DNA synthesis inhibitor.

(6) The method of distinguishing genotypes according to the above-mentioned item (1), wherein the amplification reaction solution obtained from the nucleic acid amplification step is subjected to a heat treatment prior to the competitive strand displacement reaction.

(7) The method of distinguishing genotypes according to the above-mentioned item (1), wherein the amplification reaction solution obtained from the nucleic acid amplification step is subjected to a single-stranded nucleic acid degradation treatment or a nucleotide triphosphate degradation treatment prior to the competitive strand displacement reaction.

(8) The method of distinguishing genotypes according to any one of the above-mentioned items (1) through (7), wherein; out of two nucleic acid strands constituting the reference double-stranded nucleic acid, a 3' terminal site of one strand is labeled with a first labeling substance and a 5' terminal site of another strand is labeled with a second labeling substance; the first labeling substance and the second labeling substance are substances capable of mutual energy transfer; and the level of the occurrence of strand displacement between the reference double-stranded nucleic acid and the specimen double-stranded nucleic acid is assessed by measuring a level of energy change caused by the energy transfer between the first labeling substance and the second labeling substance in the distinction step.

(9) The method of distinguishing genotypes according to the above-mentioned item (8), wherein; at least one of the first labeling substance and the second labeling substance is a fluorescent substance; the competitive strand displacement reaction in the distinction step is performed by gradually lowering the temperature of the reaction solution containing the reference double-stranded nucleic acid and the specimen double-stranded nucleic acid from a high temperature; and a level of an occurrence of strand displacement between the reference double-stranded nucleic acid and the specimen double-stranded nucleic acid is assessed based on a ratio of an amount of change in a fluorescence intensity caused by lowering the temperature of the reaction solution, to an amount of change in a fluorescence intensity caused by lowering the temperature of a control reaction solution which contains the reference double-stranded nucleic acid instead of the specimen double-stranded nucleic acid.

(10) A genotype distinguishing kit for use in the distinct of genotypes by the method of distinguishing genotypes according to the above-mentioned item (1) including: one or more substances selected from the group consisting of an extension reaction inhibitor, a single-stranded-specific nuclease, and a nucleotide triphosphatase; a nucleic acid amplification reagent for preparing the specimen double-stranded nucleic acid; and the reference double-stranded nucleic acid in which one labeling substance is introduced in a 5' terminal site of one strand of the reference nucleic acid and another labeling substance has been introduced in a 3' terminal site of another strand of the reference nucleic acid.

Effects of the Invention

With the method for distinguishing genotypes of the present invention, the accuracy and the sensitivity to discriminate genotypes are significantly improved, making it possible to distinguish with high accuracy, not only germline mutations such as SNP but also somatic mutations that have been so far difficult to distinguish with conventional types of SNP detection methods.

Moreover, with the genotype distinguishing kit of the present invention, the method for distinguishing genotypes of the present invention can be more readily carried out.

BEST MODE FOR CARRYING OUT THE INVENTION

Figure 1:
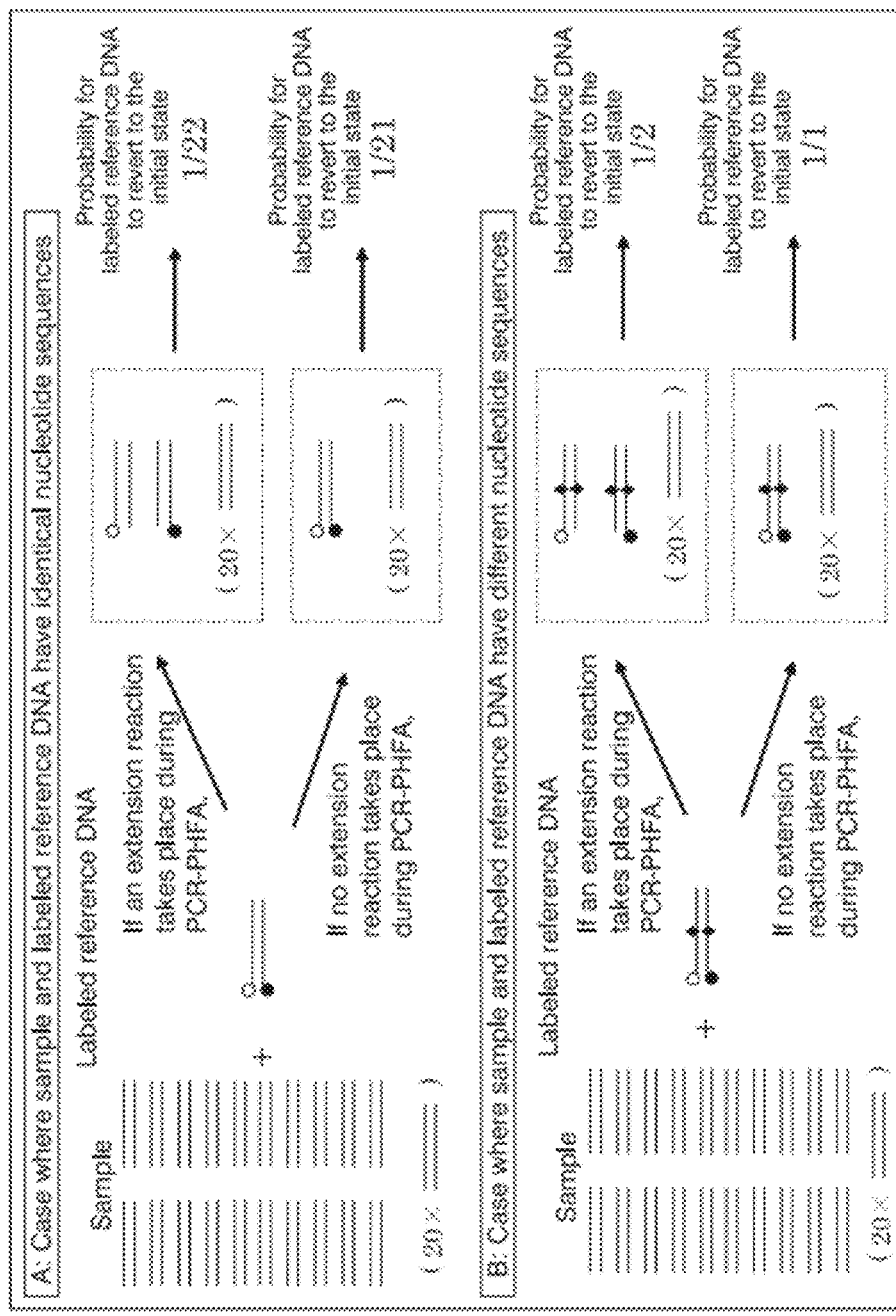
FIG. 1 is a schematic diagram showing the influence on the discrimination sensitivity in cases where a polymerase extension reaction takes place during competitive strand displacement reactions.

The term "gene mutation" used in the present invention refers to a difference of the nucleotide sequence of a gene, between individuals within a same biological species. The term "mutation site" refers to a site of difference in the nucleotide sequence. Specifically speaking, such a difference of the nucleotide sequence is caused by substitution, deletion, or insertion of one or a plurality of nucleotide(s) in the nucleotide sequence. In other words, the concept "gene mutation" of the present invention includes not only acquired mutations such as a somatic mutation, but also inherent mutations such as a SNP, a microsatellite polymorphism, and like genetic polymorphism.

In the method for distinguishing genotypes of the present invention, the term "reference double-stranded nucleic acid" refers to a double-stranded nucleic acid whose nucleotide sequence is already known to be subjected to the competitive chain displacement with a double-stranded nucleic acid derived from a specimen that serves as a target of the discrimination. Specifically speaking, the "reference double-stranded nucleic acid" means a partial region including the mutation site of the target gene, as well as being a double-stranded nucleic acid including a nucleotide sequence identical to a sequence whose mutation site is of a specific genotype. If a strand displacement reaction takes place between this reference double-stranded nucleic acid and the double-stranded nucleic acid derived from a specimen, the genotype of the gene contained in the specimen can be determined to be the same as that of the reference double-stranded nucleic acid. If no strand displacement reaction takes place, the genotype can be determined to be different from that of the reference double-stranded nucleic acid.

The method for distinguishing genotypes of the present invention is a method to improve the sensitivity to discriminate nucleotide sequences in a competitive strand displacement reaction by inhibiting the polymerase extension reaction occurring during the competitive strand displacement reaction, upon the discrimination of genotypes of a gene mutation by using a PCR-PHFA method. The reason why the sensitivity to discriminate nucleotide sequences can be improved by inhibiting the extension reaction is not clear, but could be attributed to the following theory.

In conventional types of PCR-PHFA methods, the determination of whether or not the genotype of a gene in a specimen is the same as that of the reference double-stranded nucleic acid is made by such a way that: a nucleic acid amplification reaction is performed with use of non-labeled primers and a nucleic acid in the specimen as a template; the obtained amplicon is not purified but directly mixed with a labeled reference double-stranded nucleic acid whose sequence is already known to be subjected to the strand exchange; then a competitive strand displacement reaction is performed therebetween; and the level of occurrence of the strand displacement reaction between the non-labeled nucleic acid derived from the specimen and the labeled reference double-stranded nucleic acid is assessed. Here, the reaction solution of the nucleic acid amplification reaction contains regents for carrying out the nucleic acid extension reaction such as a DNA polymerase and primers. These reagents, whose activities are kept maintained, are also mixed with the reference double-stranded nucleic acid in addition to the amplicon nucleic acid. The primers used in the nucleic acid amplification reaction are also hybridizable with the reference double-stranded nucleic acid. Thus, for example, in a case where the unpurified amplicon nucleic acid and the reference double-stranded nucleic acid are mixed, denatured by heating, and subjected to a competitive strand displacement reaction by gradually lowering the temperature, the primers hybridize with the reference double-stranded nucleic acid at a point of time when the temperature condition reaches a suitable temperature for the polymerase extension reaction, thereby producing a new extension product.

If the genotype of the gene contained in the specimen and the genotype of the reference double-stranded nucleic acid are the same, this extension product would have the same genotype as that of the non-labeled nucleic acid derived from the specimen. That is to say, even if the polymerase extension reaction takes place during the competitive strand displacement reaction, it is nothing more than a synthesis of a non-labeled nucleic acid having the same genotype as that of the non-labeled nucleic acid derived from the specimen, which can be considered to impose almost no influence on the result. In contrast, if the genotype of the gene contained in the specimen and the genotype of the reference double-stranded nucleic acid are different, a non-labeled nucleic acid having a different genotype that has never been contained in the specimen would be newly synthesized due to the occurrence of the extension reaction during the competitive strand displacement reaction, and this new nucleic acid would be present in the reaction solution. Since this non-labeled nucleic acid has been produced from the reference double-stranded nucleic acid as a template, its nucleotide sequence is exactly identical to that of the reference double-stranded nucleic acid. This acts in competition against the duplex formation into the initial state between a pair of nucleic acid strands derived from the reference double-stranded nucleic acid that have been denatured into single strands.

FIG. 1 is a schematic diagram showing the influence on the discrimination sensitivity in cases where a polymerase extension reaction takes place during competitive strand displacement reactions. In the drawing, the open circle represents a fluorescent label and the solid circle represents a quencher label for quenching the emission of fluorescence from the fluorescent label through energy transfer.

In the reaction system shown in FIG. 1, the determination of whether or not the genotype of a double-stranded nucleic acid derived from a specimen (sample) is the same as the genotype of the labeled reference double-stranded nucleic acid (labeled reference DNA) is made by detecting the fluorescence emission from the fluorescent label. If fluorescence emission from the fluorescent label is not detected from the reaction solution after the competitive strand displacement reaction, it is determined that no strand displacement took place and the labeled reference DNA has reverted to the initial state, in other words, the genotype of the sample is different from that of the labeled reference DNA. On the other hand, if fluorescence is detected, it is determined that a strand displacement took place and the labeled reference DNA has not reverted to the initial state, in other words, the genotype of the sample is the same as that of the labeled reference DNA.

In FIG. 1, the case (A) on the top illustrates a case where the genotype of the gene contained in the specimen and the genotype of the labeled reference double-stranded nucleic acid (labeled reference DNA) are the same. Assuming that the number of molecules of the double-stranded nucleic acid derived from a specimen (sample) produced by the nucleic acid amplification reaction is twenty and then one molecule of the labeled reference DNA is mixed therewith to perform the competitive strand displacement reaction, then if no extension reaction takes place during the competitive strand displacement reaction, the probability for the labeled reference DNA to revert to the initial state after the competitive strand displacement reaction is 1/21. On the other hand, if an extension reaction takes place during the competitive strand displacement reaction and a non-labeled double-stranded nucleic acid having the identical nucleotide sequence to that of the one molecule of the labeled reference DNA is produced, then the probability for the labeled reference DNA to revert to the initial state after the competitive strand displacement reaction is 1/22. In this way, because of the occurrence of the extension reaction, the probability for the labeled reference DNA to revert to the initial state decreases. However, nonetheless not so large an influence is imposed on the sensitivity to discriminate genotypes.

In FIG. 1, the case (B) on the bottom illustrates a case where the genotype of the gene contained in the specimen and the genotype of the labeled reference double-stranded nucleic acid (labeled reference DNA) are different. In the drawing, the solid diamond represents a mutation site in the labeled reference DNA (nucleotide(s) differing from the sample). Similarly to the case (A) on the top, assuming that twenty molecules of the sample are mixed with one molecule of the labeled reference DNA to perform the competitive strand displacement reaction, if no extension reaction takes place during the competitive strand displacement reaction, then the labeled reference DNA does not hybridize with the sample, and therefore the probability for the labeled reference DNA to revert to the initial state after the competitive strand displacement reaction is 1. On the other hand, if an extension reaction takes place during the competitive strand displacement reaction and a non-labeled double-stranded nucleic acid having an identical nucleotide sequence to that of the one molecule of the labeled reference DNA is produced, the newly produced extension product hybridizes with the labeled reference DNA in a competitive manner, and therefore the probability for the labeled reference DNA to revert to the initial state after the competitive strand displacement reaction remarkably decreases to ½. This results in the reduction of the amount of change between the fluorescent value in a single-stranded state before the competitive strand displacement reaction (after denaturation) and the fluorescent value in a double-stranded state after the competitive strand displacement reaction, which leads to a lowering of the sensitivity.

Moreover, the radical principle of the PCR-PHFA method is to utilize the strand displacement between a labeled reference double-stranded nucleic acid and a non-labeled double-stranded nucleic acid derived from a specimen, in which the production of a non-labeled nucleic acid that has not been derived from the specimen during the reaction is not preferable in terms of accuracy. For example, as shown in case (B) on the bottom of FIG. 1, if a strand displacement takes place between the newly produced extension product and the labeled reference DNA, fluorescence is detected from the reaction solution after the competitive strand displacement reaction, and thus a misdetermination that the genotype of the sample is the same as that of the labeled reference DNA is made. In other words, because of the occurrence of the extension reaction during the competitive strand displacement reaction, the accuracy to discriminate genotypes is lowered.

The theory, in which an extension reaction takes place during the competitive strand displacement reaction by a polymerase that has been brought in from the reaction solution of the nucleic acid amplification reaction, and as a result the accuracy and the sensitivity to discriminate the nucleotide sequences of nucleic acids are lowered, is a new finding discovered by the inventors of the present invention. Based on this finding, the present invention improves the discrimination accuracy and sensitivity through suppression of the polymerase extension reaction during the competitive strand displacement reaction.

Specifically speaking, the method for distinguishing genotypes of the present invention includes: a nucleic acid amplification step in which a mutation site-including region of a gene contained in a specimen is amplified by a nucleic acid amplification reaction, thereby obtaining an amplification reaction solution which contains a specimen double-stranded nucleic acid; and a distinction step in which the amplification reaction solution obtained from the nucleic acid amplification step is mixed with a reference double-stranded nucleic acid that is labeled with a labeling substance, and the mixture is subjected to a competitive strand displacement reaction under a condition to suppress a polymerase extension reaction, and the level of the occurrence of strand displacement between the reference double-stranded nucleic acid and the specimen double-stranded nucleic acid is assessed so as to distinguish the identity between the reference double-stranded nucleic acid and the specimen double-stranded nucleic acid.

The specimen to be supplied to the distinguishing method of the present invention can be exemplified by a bacterium, a virus, or such a pathogen, blood, sputum, a piece of diseased tissue, or such a biological matter isolated from human or like organism, feces, urine, or such excrement. Furthermore, in the case of prenatal diagnosis, it is possible to use cells of the fetus residing in amniotic fluid, or a part of dividing egg cells in a test tube, as an analyte. Moreover, these specimens can be either directly used, or if necessary, previously concentrated by collecting the sediment after centrifugal separation or such an operation, and thereafter, for example, subjected to an enzymatic treatment, a heat treatment, a surfactant treatment, an ultrasonic treatment, or a cell destruction treatment as an ensemble thereof, before use. In this case, this cell destruction treatment is conducted for the purpose of eliciting nucleic acids derived from the tissue of interest. The specific method for performing the cell destruction treatment can be performed in accordance with known methods described in documents such as PCR PROTOCOLS, Academic Press Inc., p. 14 and p. 352 (1990). In addition, it is preferable that the total amount of nucleic acids in the specimen is about 5 to 50 ng. However, it is still possible to adequately carry out the amplification with 5 ng or smaller amount.

The mutation site to be distinguished by the distinguishing method of the present invention can be exemplified by a cancer-associated gene, a hereditary disease-associated gene, a viral gene, a bacterial gene, a polymorphic gene regarded as a disease risk factor, or the like. Examples of the cancer-associated gene include the K-ras gene, the N-ras gene, the p53 gene, the BRCA1 gene, the BRCA2 gene, and the APC gene. Examples of the hereditary disease-associated gene include genes which are reportedly associated with varieties of inborn errors of metabolisms. Examples of the viral gene and the bacterial gene include genes of the hepatitis C virus and the hepatitis B virus. Examples of the polymorphic gene include genes which are not necessarily directly associated with a cause of a disease or the like but have different nucleotide sequences among individuals, such as HLA (Human Leukocyte Antigen) and a blood type-associated gene, and genes which are considered to be associated with the onset of hypertension, diabetes, or such a disease. Most of these genes are present in chromosomes of the host, although some of these genes are encoded by mitochondrial genes.

In the present invention, firstly, as the nucleic acid amplification step, a mutation site-including region of a gene contained in a specimen is amplified by a nucleic acid amplification reaction, to thereby prepare a specimen double-stranded nucleic acid. The nucleic acid amplification reaction is not specifically limited as long as the reaction is capable of amplifying the mutation site-including region into double-stranded nucleic acid molecules. The method can be appropriately selected and adopted from known nucleic acid amplification reactions such as the PCR method, the LCR (Ligase Chain Reaction) method, the 3SR (Self-sustained Sequence Replication) method, and the SDA (Strand Displacement Amplification) method (Manak, DNA Probes 2nd Edition pp. 255 to 291, Stockton Press (1993)). In particular, the PCR method is preferred for the present invention.

The specimen double-stranded nucleic acid can be prepared, for example, by designing a primer set to sandwich the mutation site-including region to be amplified, and repeatedly performing primer extension reactions with use of a polymerase. The reagents such as dNTPs and a polymerase to be used for this extension reaction can be appropriately selected and adopted from usual regents for nucleic acid amplifications. Regarding the polymerase, for example, it is possible to use an optional DNA polymerase such as the E. coli DNA polymerase I, the Klenow fragment of the E. coli DNA polymerase I, and the T4 DNA polymerase. In particular, it is preferable to use a thermostable DNA polymerase such as the Taq DNA polymerase, the Tth DNA polymerase, and the Vent DNA polymerase. By so doing, the necessity of adding fresh enzyme per each cycle can be eliminated, which can enable the automatic repetition of cycles. Furthermore, since it is possible to set the annealing temperature at 50 to 60° C., the specificity to recognize the target nucleotide sequence with primers can be improved, and thus the gene amplification reaction can be quickly and specifically performed (refer to Japanese Unexamined Patent Application, First Publication No. H01-314965, and Japanese Unexamined Patent Application, First Publication No. H01-252300, for details). Moreover, specific methods such as the reaction condition for performing this extension reaction can be performed in accordance with known methods described in Jikken Igaku (Experimental Medicine), Vol. 8, No. 9, of Yodosha Co., Ltd. (1990), PCR Technology of Stockton Press (1989), and such documents.

The specimen double-stranded nucleic acid may be an amplicon produced by amplifying a mutation site-including region of a gene so that a strand displacement reaction can take place with a reference double-stranded nucleic acid in the case where the genotype is the same as that of the reference double-stranded nucleic acid. The opposite ends of the specimen double-stranded nucleic acid are not always necessarily the same as the opposite ends of the reference double-stranded nucleic acid. For example, the difference in the chain length between the specimen double-stranded nucleic acid and the reference double-stranded nucleic acid may be approximately within 10 bases respectively per each of the opposite ends. Since the present invention is capable of improving the discrimination accuracy even if the mutation site consists of only a single base, it is preferable that the specimen double-stranded nucleic acid is a double-stranded nucleic acid produced by nucleic acid amplification of a region being completely the same as that of the reference double-stranded nucleic acid, within a mutation site-including region of a gene.

Next, as the distinction step, the amplification reaction solution obtained from the nucleic acid amplification step is mixed with the reference double-stranded nucleic acid, and the mixture is subjected to a competitive strand displacement reaction under a condition to suppress a polymerase extension reaction, and the level of the occurrence of strand displacement between the reference double-stranded nucleic acid and the specimen double-stranded nucleic acid is assessed so as to distinguish the identity between the reference double-stranded nucleic acid and the specimen double-stranded nucleic acid.

The first method to suppress the extension reaction is a method of adding an extension reaction inhibitor to a reaction solution for the competitive strand displacement reaction. By adding an extension reaction inhibitor to a reaction solution for the competitive strand displacement reaction, the extension reaction can be inhibited during the competitive strand displacement reaction without the need for any other special manipulation. Here, the extension reaction inhibitor is not specifically limited as long as it is a compound having an effect to inhibit the extension reaction without directly decomposing the polymerase, the nucleotide triphosphate, and the primers, which are needed for the extension reaction. The extension reaction inhibitor can be appropriately selected and adopted from known compounds having an effect to inhibit the extension reaction, with consideration of the type of the polymerase used in the nucleic acid amplification reaction, and the like. Such an extension reaction inhibitor can be exemplified by a chelating agent, a DNA synthesis inhibitor, or the like.

For example, the enzymatic activity of a usual PCR polymerase is susceptible to ion concentrations, especially to divalent ion concentrations. For example, magnesium ion is a divalent metal ion which is essential for DNA polymerases to exert their activities. For this reason, the extension reaction can be effectively inhibited by adding a chelating agent at a concentration that is capable of suppressing the polymerase activity, to the reaction solution for the competitive strand displacement reaction. In addition, although a method to physically remove the magnesium ion can also be considered, the manipulation is complicated. With the chelating agent, the manipulation is easy and convenient since it can be done by merely adding the chelating agent to the reaction solution for the competitive strand displacement reaction, and also the influence on the following PCR-PHFA reaction is considered to be small.

The chelating agent can be exemplified by EDTA, CDTA, DTPA, or the like. It is possible to determine the dose of the chelating agent in an experimental manner with consideration of the type of the chelating agent, the type of the polymerase, and the like. For example, when EDTA is used as the chelating agent, it is preferable to add it so that the EDTA concentration in the reaction solution of the competitive strand displacement reaction is 15 mM or higher. The preferred range of the EDTA concentration is from 15 mM to 100 mM, and a more preferred range is from 25 mM to 50 mM.

In addition, it is also possible to inhibit the extension reaction by adding an enzyme inhibitory substance to the reaction solution for the competitive strand displacement reaction. Generally speaking, examples of the substance to inhibit the activity of a DNA polymerase are DNA synthesis inhibitors. The DNA synthesis inhibitors are largely classified into two types: substances which bind to a DNA polymerase and inhibit the activity of the polymerase; and substances which bind to DNA and inhibit the DNA synthesis. In the present invention, when a substance which binds to DNA is used, the PCR-PHFA reaction itself might be inhibited. For this reason, it is preferable to use a DNA synthesis inhibitor which binds to a DNA polymerase. In addition, it is also possible to inhibit the activity of a DNA polymerase by adding an anionic protein which binds to the DNA polymerase. That is, an anionic protein which binds to a polymerase can also be used as an extension reaction inhibitor.

The second method to suppress the extension reaction is a method of heat-treating the amplification reaction solution after the nucleic acid amplification reaction. By heat-treating the amplification reaction solution after the nucleic acid amplification reaction, the polymerase contained in the amplification reaction solution can be deactivated. In general, heat resistant DNA polymerases are used for PCR reactions, and these polymerases are often deactivated by a treatment at 95° C. or higher temperature for 10 minutes or longer. Since the stability of a heat resistant DNA polymerase with respect to heat depends on each enzyme, the temperature and the duration of the heat treatment can be appropriately set with consideration of the type of enzyme for use in the nucleic acid amplification reaction. For example, among heat resistant DNA polymerases, usual Taq DNA polymerases have relatively weak heat resistance. If the specimen has been prepared by performing a PCR reaction with use of such an enzyme, it is relatively easily possible to avoid new extension reactions by this heat treatment.

The heat treatment of the amplification reaction solution can be conducted either before or after mixing it with the reference double-stranded nucleic acid, as long as it is conducted prior to the competitive strand displacement reaction. If the heat treatment is conducted after the mixing, both the reference double-stranded nucleic acid and the specimen double-stranded nucleic acid can be denatured by this heat treatment, and thus there is no need of performing any other denaturation operation.

The third method to suppress the extension reaction is a method of degrading or deactivating (denaturing) a substance or the like needed for the extension reaction in the amplification reaction solution. Specific examples of such a method include methods to subject the amplification reaction solution to a single-stranded nucleic acid degradation treatment or to a nucleotide triphosphate degradation treatment.

The primers needed for the extension reaction are left remaining in the amplification reaction solution, and these primers hybridize with the reference double-stranded nucleic acid. This leads to an extension reaction. Here, the extension reaction can be suppressed by subjecting the amplification reaction solution to a single-stranded nucleic acid degradation treatment so as to degrade these primers. Specifically speaking, the single-stranded nucleic acid degradation treatment can be conducted by adding a single-strand specific nuclease to the amplification reaction solution to produce an enzymatic reaction. Although the specimen double-stranded nucleic acid is contained in the amplification reaction solution, it is a double-stranded nucleic acid. Therefore, with use of the single-strand specific nuclease, it is possible to selectively degrade only the primers to eliminate their functions as primers.

The single-stranded nucleic acid degradation treatment can be conducted either before or after mixing it with the reference double-stranded nucleic acid, as long as it is conducted prior to the competitive strand displacement reaction. This is because the reference double-stranded nucleic acid is also nondegradable by the single-strand specific nuclease. Note that, however, the single-strand specific nuclease activity in the reaction solution for the competitive strand displacement reaction should be deactivated before the denaturation treatment of the competitive strand displacement reaction. The purpose of doing so is to avoid degradation of the specimen double-stranded nucleic acid and the reference double-stranded nucleic acid that have been separated into single strands by the denaturation treatment. Therefore, in the single-stranded nucleic acid degradation treatment, it is preferable to use a type of single-strand specific nuclease which would be deactivated at the high temperature at which the double-stranded nucleic acids are denatured. Such a nuclease can be exemplified by the exonuclease I, the exonuclease T, the mung bean nuclease, or the like.

In addition, four types of deoxynucleoside triphosphates, serving as substrates needed for the extension reaction, are also left remaining in the amplification reaction solution. They lose their activities as the substrates when degraded into deoxynucleoside monophosphates. Therefore, the extension reaction can also be suppressed by subjecting the amplification reaction solution to a nucleotide triphosphate degradation treatment so as to degrade the deoxynucleoside triphosphates into deoxynucleoside monophosphates. The enzyme to convert the deoxynucleoside triphosphates into deoxynucleoside monophosphates can be exemplified by apyrase or the like.

It is considered that the polymerase extension reaction can be avoided by purifying the double-stranded nucleic acids that have been produced by the nucleic acid amplification reaction, before conducting the PCR-PHFA reaction. However, the purification takes time and labor, and also could be a cause of contamination because the amplicons may be spread out. Thus, this method cannot be said to be suitable for the site of diagnosis. In the present invention, it is possible to suppress new extension reactions with easier manipulation, as with of the above-mentioned three methods.

The competitive strand exchange reaction is a competitive displacement reaction of nucleic acid strands occurring between a double-stranded nucleic acid and a single-stranded nucleic acid whose nucleotide sequences are homologous, or between a double-stranded nucleic acid and a double-stranded nucleic acid whose nucleotide sequences are homologous (competitive hybridization). This can be conducted by annealing after the denaturation of the reference double-stranded nucleic acid and the specimen double-stranded nucleic acid.

The method for denaturing the reference double-stranded nucleic acid and the specimen double-stranded nucleic acid is preferably carried out by heating or by using an alkali. Because the present invention is easy and convenient, it is preferable to denature them by heating. Specifically speaking, the double-stranded nucleic acids can be denatured by heating at 90 to 100° C., and preferably at 95 to 100° C., for a predetermined period of time. The timing to mix the reference double-stranded nucleic acid and the specimen double-stranded nucleic acid may be either right before the denaturation or after the denaturation.

Upon the annealing of the denatured reference double-stranded nucleic acid and specimen double-stranded nucleic acid, it is preferable to adjust the salt concentration in the reaction solution to be optimum. The optimum salt concentration is usually dependent on the chain length. In general, hybridization uses SSC (20×SSC: 3M sodium chloride and 0.3M sodium citrate) or SSPE (20×SSPE: 3.6M sodium chloride, 0.2M sodium phosphate, and 2 mM EDTA). The distinguishing method of the present invention can also use such a solution by diluting at a suitable concentration. Moreover, if necessary, it is also possible to add an organic solvent such as dimethyl sulfoxide (DMSO) and dimethyl formamide (DMF).

When denaturation has been done by heating, annealing can then be conducted by gradually lowering the temperature of the reaction solution from a high temperature (which is in general the denaturation temperature, for example, a given temperature within a range from 90 to 100° C.) to carry out the competitive strand exchange reaction. The speed of lowering the temperature of the reaction solution, the temperature of the reaction solution at the time of the completion of the reaction, and such conditions, can be appropriately set according to the chain lengths and the nucleotide sequences of the reference double-stranded nucleic acid and the specimen double-stranded nucleic acid. The slower the speed of lowering the temperature of the reaction solution, the more it is possible to reduce the probability of hybridization between single strands whose nucleotide sequences are not complementary to each other. For example, the competitive strand exchange reaction can be accurately performed by lowering the temperature at a speed of 0.1° C./minute to 0.3° C./minute within a range from 98 to 50° C., and more preferably at a speed of 0.1° C./minute within a range from 98 to 70° C.

In the present invention, the reference double-stranded nucleic acid is labeled with a labeling substance while the specimen double-stranded nucleic acid is prepared without labeling. The level of the occurrence of strand displacement between the reference double-stranded nucleic acid and the specimen double-stranded nucleic acid can be assessed by seeing the indication from the label. For example, a case is assumed in which, out of two nucleic acid strands constituting the reference double-stranded nucleic acid, one strand is labeled with a certain type of labeling substance while the other strand is labeled with a different type of labeling substance. In this case, if no strand displacement reaction took place, these two types of labeling substances are both detected from the same kind of molecules. On the other hand, if a strand displacement reaction took place, there exists a kind of molecule from which only either one of these two types of labeling substances is detected. Accordingly, the level of the occurrence of strand displacement between the reference double-stranded nucleic acid and the specimen double-stranded nucleic acid can be assessed by detecting which type(s) of labeling substance(s) is/are labeled on the respective molecules of the double-stranded nucleic acids in the reaction solution.

The labeling substance may be either nonradioactive or radioactive, although preferred is a nonradioactive substance. Examples of the nonradioactive labeling substance, when it comes to directly labelable ones, can be given by fluorescent substances (for example, fluorescein derivatives such as fluorescein isothiocyanate, rhodamine and its derivatives such as tetramethylrhodamine isothiocyanate, and the like), and chemiluminescent substances (for example, acridine and the like). Moreover, it is also possible, by using a substance that is specifically bindable to a labeling substance, to detect the labeling substance in an indirect manner. Examples of such a labeling substance can be given by biotin, a ligand, a specific type of nucleic acid or protein, and a hapten. Examples of the substance that is specifically bindable to a labeling substance can be given by: avidin/streptavidin that is specifically bindable to biotin in cases where the labeling substance is biotin; an antibody that is specifically bindable to a hapten in cases where the labeling substance is the hapten; a receptor in cases where the labeling substance is a ligand; and a nucleic acid that is specifically bindable to a specific type of nucleic acid or protein, a nucleic acid-binding protein, or a protein which has an affinity with a specific type of protein, in cases where the labeling substance is the specific nucleic acid or protein. It is possible to use a compound having a 2,4-dinitrophenyl group or digoxigenin, as the hapten mentioned above. Furthermore, it is also possible to use biotin, a fluorescent substance, or the like, as the hapten. These labeling substances can be introduced either solely, or if necessary, as a combination of a plurality of types, by a known means (refer to Japanese Unexamined Patent Application, First Publication No. S59-93099, Japanese Unexamined Patent Application, First Publication No. S59-148798, and Japanese Unexamined Patent Application, First Publication No. S59-204200).

In addition, in cases where a substance that is bindable to a solid phase carrier is employed as either one of these two types of labeling substances for labeling the reference double-stranded nucleic acid, the level of the occurrence of strand displacement between the reference double-stranded nucleic acid and the specimen double-stranded nucleic acid can be assessed by usual manipulation for solid-liquid separation. For example, a case is assumed in which one strand of the reference double-stranded nucleic acid is labeled with a labeling substance A, the other strand is labeled with a labeling substance B that is bindable to a solid phase carrier, and the reaction solution after the strand displacement reaction is contacted to the solid phase carrier that is bindable to the labeling substance B. Thereafter, the labeling substance A in the double-stranded nucleic acids which bind to the solid phase carrier is measured. If a strand displacement reaction takes place, the proportion of the double-stranded nucleic acid labeled by the labeling substance A in the entire double-stranded nucleic acids which bind to the solid phase carrier decreases.

In particular, in the present invention, it is preferable to use two types of labeling substances capable of mutual energy transfer (for example, a donor labeling substance which emits fluorescence by excitation and an acceptor labeling substance which absorbs the fluorescence), to assess the level of the occurrence of strand displacement between the reference double-stranded nucleic acid and the specimen double-stranded nucleic acid by seeing the indication of the level of energy change caused by the energy transfer between these labeling substances.

The term "energy transfer between labeling substances" used in the present invention refers to a transfer of energy from a donor labeling substance which generates energy to an acceptor labeling substance which receives the energy generated from this donor labeling substance, when at least these two types of labeling substances are close to each other. For example, in a case where the two types of labeling substances are fluorescent substances, the acceptor labeling substance absorbs fluorescence that has been generated by the excitation of the donor labeling substance, and the fluorescence emitted from this acceptor labeling substance is measured. Alternatively, it is also possible to measure the fluorescence that has been generated by the excitation of the donor labeling substance, by seeing the quenching of the donor labeling substance caused by the absorption of the acceptor labeling substance (PCR Methods and Applications 4, 357-362 (1995), Nature Biotechnology 16, 49-53 (1998)). The energy transfer may take place sometimes even if the fluorescence wavelength of the donor labeling substance and the absorption wavelength of the acceptor labeling substance are not overlapped. Such energy transfer can also be included in the scope of the present invention.

Specifically speaking, what is used is a reference double-stranded nucleic acid, in which, out of two nucleic acid strands constituting the reference double-stranded nucleic acid, a 3' terminal site of one strand is labeled with a first labeling substance and a 5' terminal site of another strand is labeled with a second labeling substance that is capable of mutual energy transfer with the first labeling substance. Either one of the first labeling substance and the second labeling substance may be a donor labeling substance. Since this reference double-stranded nucleic acid is in a state where the first labeling substance and the second labeling substance are close to each other, the energy transfer occurs. On the other hand, if a competitive strand displacement reaction with the specimen double-stranded nucleic acid takes place, the double-stranded nucleic acid which has undergone the strand displacement does not create the energy transfer since the first labeling substance and the second labeling substance are apart from each other, thus reducing the proportion of the double-stranded nucleic acid creating the energy transfer in the reaction solution. Therefore, by measuring the energy generated from the first labeling substance or the second labeling substance (the fluorescence intensity in a case of a fluorescent substance), it is possible to assess the level of energy change caused by the energy transfer, so as to thereby assess the level of the occurrence of strand displacement between the reference double-stranded nucleic acid and the specimen double-stranded nucleic acid.

A pair of nucleic acid strands having the same genotype (having completely complementary nucleotide sequences) forms a duplex preferentially over a pair of nucleic acid strands having different genotypes (having different nucleotide sequences at the mutation site). For this reason, by measuring the level of energy change caused by the energy transfer between the labeling substances in association with the above-mentioned phenomenon, in other words, by measuring the level of energy change caused by the created or quenched energy transfer due to the strand displacement reaction, with a given detector, it is possible to detect whether or not the genotype of the mutation site of the gene contained in a specimen is the same as that of the reference double-stranded nucleic acid, or to detect the proportion of the genotype which is the same as that of the reference double-stranded nucleic acid in the specimen. For example, when fluorescence energy transfer is utilized for the detection, the presence or absence of, or the proportion of, the gene having the same genotype as that of the reference double-stranded nucleic acid can be readily detected by measuring the fluorescent spectrum within specific wavelengths by a spectrofluorimeter, a fluorescence plate reader, or the like.

Figure 2A:
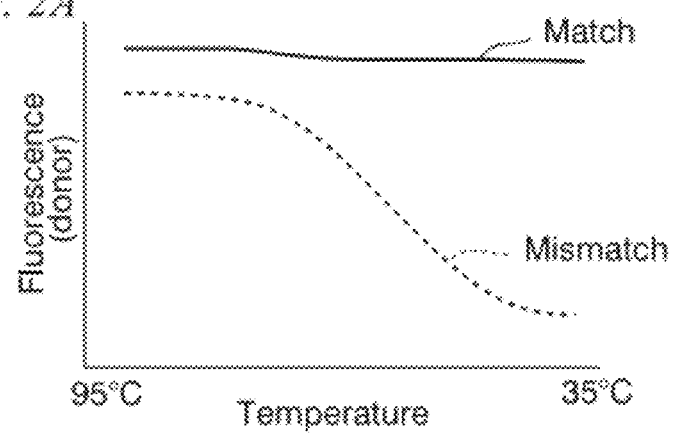
FIG. 2A is a schematic diagram showing the behavior of the fluorescence intensity of respective labeling substance in cases where the non-labeled specimen double-stranded nucleic acid and the reference double-stranded nucleic acid that is labeled with the donor labeling substance and the acceptor labeling substance are mixed, denatured, and then subjected to a gradual lowering of the temperature.
Figure 2B:
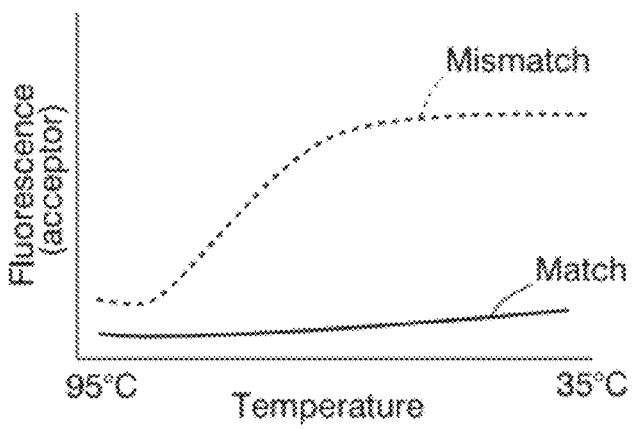
FIG. 2B is a schematic diagram showing the behavior of the fluorescence intensity of respective labeling substance in cases where the non-labeled specimen double-stranded nucleic acid and the reference double-stranded nucleic acid that is labeled with the donor labeling substance and the acceptor labeling substance are mixed, denatured, and then subjected to a gradual lowering of the temperature.

FIG. 2A and FIG. 2B are schematic diagrams showing the behavior of the fluorescence intensity of the donor labeling substance (FIG. 2A) and the behavior of the fluorescence intensity of the acceptor labeling substance (FIG. 2B) in cases where the non-labeled specimen double-stranded nucleic acid and the reference double-stranded nucleic acid having one strand labeled with the donor labeling substance on the 3' terminal site and the other strand labeled with the acceptor labeling substance on the 5' terminal site are mixed, denatured, and then subjected to a gradual lowering of the temperature. In these diagrams, the symbol "Match" shows the behavior in the case where the reference double-stranded nucleic acid and the specimen double-stranded nucleic acid have the same genotype, while the symbol "Mismatch" shows the behavior in the case where their genotypes are different from each other.

In this way, by assessing the level of the occurrence of strand exchange between the reference double-stranded nucleic acid and the specimen double-stranded nucleic acid through the measurement of the level of energy change caused by the energy transfer between the labeling substances, it is possible to quickly, easily, and conveniently determine whether the reference double-stranded nucleic acid and the specimen double-stranded nucleic acid are identical or not, without the need for complicated manipulation for solid-liquid separation or the like. Furthermore, by introducing both the labeling substances respectively into the 3' terminal site and the 5' terminal site which are positioned close to each other, it is possible to accurately and reliably understand the level of the occurrence of strand displacement, and in addition, even if the reference double-stranded nucleic acid or the specimen double-stranded nucleic acid is a long gene fragment in the chain length, it is always possible to accurately and reliably assess the level of the displacement between complementary strands with excellent sensitivity, and it is also possible to accurately and stably distinguish the identity of genotypes. In particular, since this is an easy method which does not require any complicated manipulation for solid-liquid separation that has been so far required for conventional methods, it is possible to achieve automatization to respond to the demands from the clinical site on the front line.

There are no specific limitations in the labeling substances that can be used as the first labeling substance and the second labeling substance, as long as they are capable of energy transfer when positioned close to each other. Particularly preferred are fluorescent substances and delayed fluorescent substances. Depending on some cases, chemiluminescent substances, bioluminescent substances, and the like, may also be used. Examples of the combination of such labeling substances include: a combination of a fluorescein or a derivative thereof (such as fluorescein isothiocyanate) with a rhodamine or a derivative thereof (such as tetramethylrhodamine isothiocyanate or tetramethylrhodamine-5- (and -6-)hexanoic acid); a combination of a fluorescein with a dabsyl; and the like. Any combination can be selected from these examples (Nonisotopic DNA Probe Techniques. Academic Press (1992)). Moreover, it is also possible to employ a combination of molecules that are capable of heat energy radiation when positioned close to each other. Examples of the combination of such labeling substances include combinations of either BHQ (registered trademark, Black hole quencher)-1 or BHQ (registered trademark)-2 with a substance selected from the group consisting of Alexa Fluor (registered trademark) 488 (a product of Invitrogen), ATTO 488 (a product of ATTO-TEC GmbH), Alexa Fluor (registered trademark) 594 (a product of Invitrogen), and ROX (Carboxy-X-rhodamine).

Regarding the method to introduce the first labeling substance or the second labeling substance into the reference double-stranded nucleic acid, a usual method of introducing a label into a nucleic acid can be employed. Examples thereof can include: a method of introducing a labeling substance into a nucleic acid in a direct chemical manner (Biotechniques 24, 484-489 (1998)), a method of introducing a mononucleotide binding with a labeling substance through a DNA polymerase reaction or an RNA polymerase reaction (Science 238, 336-3341 (1987)), and a method of introducing through a PCR reaction with use of a primer which has a labeling substance introduced therein (PCR Methods and Applications 2, 34-40 (1992)).

The position to introduce the labeling substance in the reference double-stranded nucleic acid has to be a position at which an energy transfer can be created or quenched by the strand displacement reaction, in other words, a 3' terminal site or a 5' terminal site of the nucleic acid strand. Specifically speaking, the terms "5' terminal site" and "3' terminal site" used in the present invention respectively refer to ranges within 30 bases from the 5' end and the 3' end of the nucleic acid strand. However, since it becomes easier to create the energy transfer if both the labeling substances are closer, preferred are within 10 bases respectively from these ends, and most preferred are the 5' end and the 3' end. Here, it might be impossible to detect a single nucleotide or such a small displacement if too many labeling substances have been introduced into sites of nucleotides to hybridize with complementary strands. Therefore, it is preferable to introduce them into only the terminal sites of respective nucleic acid strands. For example, by introducing one of these two types of labeling substances into the 5' terminal site (3' terminal site) of one nucleic acid strand, as well as introducing the other type of labeling substance into the 3' terminal site (5' terminal site) of the other nucleic acid strand which is complementary thereto, both the nucleic acid strands can create or quench an energy transfer through the strand displacement reaction without imposing an influence on the hybridization reaction.

Specifically speaking, in order to prepare a nucleic acid strand having a label on the 5' terminal site, it is possible to employ: a method of binding an oligonucleotide, in which a labeling substance has been introduced into the 5' terminal site, to an optional nucleic acid strand by a ligase (Nucleic Acids Res. 25, 922-923 (1997)); a method of performing a PCR reaction with use of a primer in which a labeling substance has been introduced into the 5' terminal site (PCR Methods and Applications 2, 34-40 (1992)), or the like.

On the other hand, in order to prepare a nucleic acid strand having a label on the 3' terminal site, it is possible to employ a method of binding an oligonucleotide, in which a labeling substance has been introduced into the 3' terminal site, to an optional nucleic acid strand by a ligase, as with the above-mentioned case of introducing a labeling substance into the 5' terminal site. In cases where the nucleic acid strand is not DNA but RNA, or in cases where the 3' terminal site of DNA is RNA, the ring of the sugar (ribose) at the end of the RNA can be selectively opened and the resultant aldehyde group can be utilized for the labeling.

Furthermore, it is also possible to introduce a mononucleotide triphosphate, in which a labeling substance has been introduced, into the 3' terminal site of the nucleic acid strand with the aid of the action of terminal deoxynucleotidyl transferase (Biotechniques 15, 486-496 (1993)).

If the reference double-stranded nucleic acid is a relatively short nucleic acid strand of 100 bases or shorter, the reference nucleic acid can be prepared by direct chemical synthesis (Nucleic Acids Res. 16, 2659-2669 (1988), and Bioconjug. Chem. 3, 85-87 (1992)).

The reference double-stranded nucleic acid can be prepared by a nucleic acid amplification reaction with use of, as a template, a nucleic acid whose nucleotide sequence is already known to have a desired genotype at the mutation site. The nucleic acid amplification reaction of this case can be appropriately selected and adopted from known nucleic acid amplification reactions, as with the case for preparing the specimen double-stranded nucleic acid. In particular, the PCR method is preferred for the present invention. Furthermore, the mass preparation can be achieved by inserting an amplicon from the nucleic acid amplification reaction into a vector, which is selected from a plasmid vector, a phage vector, or a chimera vector consisting of a plasmid and a phage, and transfecting it into any growable host such as bacteria like *Escherichia coli* and *Bacillus subtilis*, or yeast (gene cloning).

Moreover, the reference double-stranded nucleic acid can be prepared by, for example, known chemical synthesis. The method of chemical synthesis can be exemplified by the triester method, the phosphite method, or the like. For example, the double-stranded DNA can be prepared in such a way that a large amount of single-stranded DNA is prepared by using a usual automatic synthesizer (such as 392 of APPLIED BIOSYSTEMS or the like) that employs a solid phase synthesis method with an insoluble carrier, and thereafter the thus prepared single-stranded DNA is subjected to annealing.

In general, the level of energy change caused by the energy transfer between labeling substances can be assessed by measuring the fluorescence emission from a labeling substance. This fluorescence measurement often uses a so-called real-time PCR system which is capable of simultaneous analysis of a large number of analytes and capable of variously controlling the temperature. However, such a system is not always high in the fluorescence measurement accuracy per detection, and often shows a large deviation between respective wells. Moreover, a deviation in the dose of the reference double-stranded nucleic acid to be added may also be a cause to significantly affect the measurement accuracy. Accordingly, upon quantitative measurements, it is preferable to compensate the deviation across these measurements.

In the detection method utilizing the fluorescence resonance energy transfer, generally performed is a method in which the deviation across measurements is compensated by obtaining the ratio between the fluorescent values of both the donor fluorescent substance and the acceptor fluorescent substance. In other words, it is a method in which both the fluorescence emitted by the excitation of the donor and the fluorescence emitted by the excitation of the acceptor due to the energy transfer from the donor are measured, and the ratio therebetween is obtained. Therefore, the inventors of the present invention have examined whether or not it is possible to reduce the deviation by obtaining the ratio between the fluorescent value of the donor labeling substance and the fluorescent value of the acceptor labeling substance after the strand exchange reaction (at the end point), in the assay of the level of energy change caused by the energy transfer between the labeling substances in the method for distinguishing genotypes of the present invention. However, as shown in Example 6 that will be described later, it is not possible to adequately compensate the deviation by this method. This can be attributed to the reason that: the fluorescent value of the donor labeling substance after the strand exchange reaction is so very small that the deviation across fluorescence measurements under such a situation is prone to be very large, which ends up with a large deviation in the value of the ratio between the fluorescent value of the donor labeling substance and the fluorescent value of the acceptor labeling substance. In addition, the reason why the fluorescent value of the donor labeling substance is small is that: if no strand exchange reaction took place and the denatured reference double-stranded nucleic acid has reverted to the original double-stranded nucleic acid, the energy transfer is created and therefore most of the fluorescence of the donor labeling substance undergoes the energy transfer to the acceptor labeling substance, as a result of which the light emission is very weak.

Therefore, the inventors of the present invention have conducted further examinations. As a result, they have discovered that the deviation across measurements can be well compensated by making a comparison between the amounts of change in the fluorescence intensity caused by lowering the temperature of reaction solutions, in other words, making a comparison between the amount of change $\Delta F$ (fluorescence) of a reaction solution (specimen reaction solution) which contains a specimen double-stranded nucleic acid with the amount of change $\Delta F$ of a reaction solution (control reaction solution) which does not contain the specimen double-stranded nucleic acid, wherein the $\Delta F$ value is given by subtraction of the fluorescence intensity in the annealed double-stranded state of nucleic acid from the fluorescence intensity in the denatured single-stranded state.

The $\Delta F$ value may be the amount of change of the donor labeling substance, or may be the amount of change of the acceptor labeling substance. Specifically speaking, the $\Delta F$ value of the donor labeling substance can be determined by the following Equation (1). Likewise, the $\Delta F$ value of the acceptor labeling substance can be determined by the following Equation (2). In these Equations (1) and (2), the symbol "F[start-point]" refers to the fluorescence intensity at a temperature at the time of the initiation of the lowering of the temperature of the reaction solution, and the symbol "F[end-point]" refers to the fluorescence intensity at a temperature at the time of the completion of the lowering of the temperature of the reaction solution.

[Formula 1]

$$\Delta F = F[\text{start-point}] - F[\text{end-point}] \quad (1)$$

$$\Delta F = F[\text{end-point}] - F[\text{start-point}] \quad (2)$$

In addition, the $\Delta F$ value can also be obtained by the following Equation (3), using either the donor labeling substance or the acceptor labeling substance. In the following Equation (3), the "symbol F[max]" refers to the maximum fluorescence intensity within the temperature-dependent behavior of the fluorescence throughout the initiation to the completion of the lowering of the temperature of the reaction solution. Likewise, the symbol F[min] refers to the minimum fluorescence intensity within the temperature-dependent behavior of the fluorescence.

[Formula 2]

$$\Delta F = F[\text{max}] - F[\text{min}] \quad (3)$$

Figure 3:
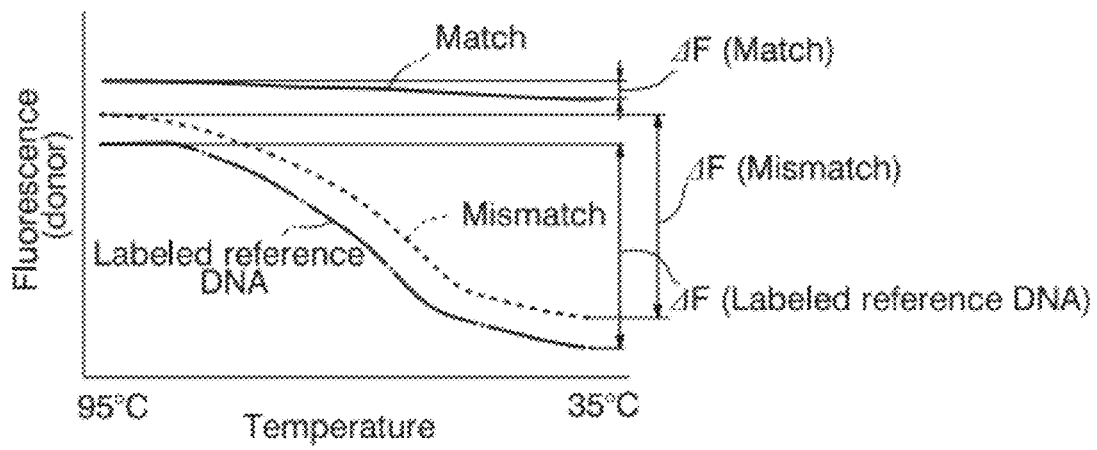
FIG. 3 is a diagram illustrating how to obtain the ΔF value from the behavior of the fluorescence intensity of the donor labeling substance.

FIG. 3 is a diagram illustrating how to obtain the $\Delta F$ value from the behavior of the fluorescence intensity of the donor labeling substance. In the diagram, the symbol "Match" shows the behavior in the case where the reference double-stranded nucleic acid and the specimen double-stranded nucleic acid have the same genotype, the symbol "Mismatch" shows the behavior in the case where their genotypes are different from each other, and the symbol "Labeled reference DNA" shows the behavior in the case where the specimen double-stranded nucleic acid is not contained (control reaction solution).

Specifically speaking, the comparison of the ΔF value caused by lowering the temperature of the reaction solution with the ΔF value caused by lowering the temperature of the control reaction solution can be made by obtaining the Index value (%) given by the following Equation (4).

[Formula 3]

$$\text{Index value (\%)} = \Delta F[\text{reaction solution}]/\Delta F[\text{control reaction solution}] \times 100 \quad (4)$$

If no strand exchange reaction takes place and the denatured reference double-stranded nucleic acid has reverted to the initial duplex, the fluorescence from the donor labeling substance after the strand exchange reaction is weak, and in addition, the fluorescence from the acceptor labeling substance in a single-stranded state is also weak. However, it was found that, even in such a situation, the deviation in the difference from the fluorescent value of the donor labeling substance in the single-stranded state before the competitive strand displacement reaction, or the difference from the fluorescent value of the acceptor labeling substance in the double-stranded state after the competitive strand displacement reaction, is not so large as compared to the case of obtaining the ratio between the fluorescent value of the donor labeling substance and the fluorescent value of the acceptor labeling substance, and the deviation across measurements can be well compensated.

The level of the occurrence of exchange between the reference double-stranded nucleic acid and the specimen double-stranded nucleic acid can be calculated by setting the level of the fluorescence resonance energy transfer of the labeled double-stranded nucleic acid alone, namely, ΔF[control reaction solution], to be 100%. In the case where the strand exchange reaction is performed by mixing the reference double-stranded nucleic acid and the specimen double-stranded nucleic acid, an Index value close to 100% indicates that no strand exchange took place, and thus the determination is made such that the genotype of the specimen double-stranded nucleic acid is different from that of the reference double-stranded nucleic acid. On the other hand, an Index value close to 0% indicates that the strand exchange took place, and thus the determination is made such that the genotype of the specimen double-stranded nucleic acid is the same as that of the reference double-stranded nucleic acid.

Furthermore, the inventors of the present invention have also examined the shortening of the reaction time required for the competitive strand displacement reaction. As described above, it has been deemed to be important for the PCR-PHFA method to denature the mixture of the specimen double-stranded nucleic acid and the reference double-stranded nucleic acid at a high temperature and then slowly lower the temperature (refer to Oka, T., Nucleic Acids Res., 1994, Vol. 22, pp. 1541-1547). However, quick tests have been in demand for actual tests. So, shortening of the reaction time is an important task. For example, Patent Document 1 describes that the condition of lowering the temperature at a rate of 1° C. per 3 to 10 minutes within a range from 98° C. to 58° C. can be suggested as a guideline. In this case, the reaction time is about 120 minutes to 400 minutes, meaning that it takes an extremely long time.

The inventors of the present invention came to consider that the strand displacement reaction takes place at or above a certain level of defined temperature and the slow temperature change is important within this range in the PCR-PHFA method. In addition, when the reference double-stranded nucleic acid is labeled with the donor labeling substance and the acceptor labeling substance, it is considered to be possible to estimate the range where the strand displacement reaction takes place by assessing the fluctuation of the fluorescence intensity during the gradual lowering of the temperature after denaturation of the reference double-stranded nucleic acid. Shortening of the reaction time without sacrificing the discrimination accuracy becomes possible by adequately slowing down the cooling rate of the reaction solution within this range where the strand displacement reaction takes place while accelerating the cooling rate in other temperature ranges. The range where the strand displacement reaction takes place is in the vicinity of the inflection point of the fluorescence intensity fluctuation (a temperature at which the average rate of change of the fluorescence intensity relative to the temperature is maximum), and this inflection point of the fluorescence intensity fluctuation can be obtained by calculating the differential value of the fluorescence intensity at each temperature (dF/dT: F represents the fluorescent value and T represents the time). This inflection point generally corresponds to the Tm value, which is used as a reference of the melting temperature of a double-stranded nucleic acid. It is considered that the Tm value differs depending on the length of the double-stranded nucleic acid, the nucleotide sequence, the composition of the solution, and the like. In the present invention, the range of the temperature change can be set by obtaining the inflection point of the competitive strand displacement reaction of the reference double-stranded nucleic acid in the reaction solution, and adopting a temperature corresponding thereto as a guideline. Moreover, the rate of the temperature change can be accelerated within a range where genotypes can be adequately distinguished. The difficulty or easiness to distinguish genotypes is dependent on the nucleotide sequence, and the estimation is quite difficult. Therefore, the acceleration should be performed by learning with trial and error with discriminations of mutations as a guideline.

The method for distinguishing genotypes of the present invention so excels in the accuracy to discriminate genotypes that it possible to distinguish not only germline mutations such as SNP but also somatic mutations seen in cancer cells and the like with adequate accuracy. Therefore, the method is extremely useful for clinical tests and the like.

The genotype distinguishing kit of the present invention is a kit for use in the discrimination of the genotype of a gene mutation contained in a specimen, or the detection of the content proportion of a specific genotype, according to the method for distinguishing genotypes of the present invention, wherein the kit includes: one or more substances selected from the group consisting of an extension reaction inhibitor, a single-stranded-specific nuclease, and a nucleotide triphosphatase; and a nucleic acid amplification reagent for preparing the specimen double-stranded nucleic acid. It is also preferable that the kit further includes a combination of two types of labeling substances capable of mutual energy transfer, a reagent for introducing one of the labeling substances into a 3' terminal site of the nucleic acid strand, and a reagent for introducing the other labeling substance into a 5' terminal site of the nucleic acid strand. In addition, it is also possible to have a combination of a cell lysis reagent for pretreating the specimen, a reagent for detecting the indication of the labeling substance, and the like. In this way, by having such regents necessary for the method for distinguishing genotypes of the present invention in a kit set, genotypes can be more easily and conveniently distinguished in a shorter time.

EXAMPLES

Hereunder is a specific description of the present invention with reference to Examples. However, the present invention is not to be limited by the following Examples.

In Examples 1 to 6, the codon 12 or codon 13 mutation in the K-ras oncogene was the mutation site to be distinguished. Moreover, labeled reference double-stranded nucleic acids having respective genotypes at the mutation site (hereunder, referred to as "labeled reference DNA") were prepared in accordance with usual oligonucleotide chemical synthesis method. Out of two strands of each labeled reference DNA, one strand was labeled with FAM (a product of Glen Research Corp.) at the 5' end, and the other strand was labeled with Alexa (a product of Invitrogen) at the 3' end. Table 1 shows the sequences of the thus chemically synthesized DNA strands per respective genotypes. In Table 1, the codons 12 and 13 are indicated by the underline, and the mutation sites are indicated by lowercase letters. Moreover, the symbol "Wild" represents the wild-type, the symbol "G12S" represents the genotype in which the first nucleotide in the codon 12 was mutated from guanine to adenine, the symbol "G12R" represents the genotype in which the first nucleotide in the codon 12 was mutated from guanine to cytosine, the symbol "G12C" represents the genotype in which the first nucleotide in the codon 12 was mutated from guanine to thymine, the symbol "G12D" represents the genotype in which the second nucleotide in the codon 12 was mutated from guanine to adenine, the symbol "G12A" represents the genotype in which the second nucleotide in the codon 12 was mutated from guanine to cytosine, the symbol "G12V" represents the genotype in which the second nucleotide in the codon 12 was mutated from guanine to thymine, and the symbol "G13D" represents the genotype in which the second nucleotide in the codon 13 was mutated from guanine to adenine. Furthermore, the symbol denoted by "-FAM" at the end of each genotype refers to a DNA strand having its 5' end labeled with FAM, and the symbol denoted by "-Ale" refers to a DNA strand having its 3' end labeled with Alexa. The number in the right column shows the sequence number corresponding to the Sequence Listing.

TABLE 1

| Genotype | Nucleotide sequence | | | |
|---|---|---|---|---|
| Wild-FAM | TATAAACTTGTGGTAGTTGGAGCT | GGTGGC | GTAGGCAAGAGTGCCTTGACGATA | 1 |
| Wild-Ale | TATCGTCAAGGCACTCTTGCCTAC | GCCACC | AGCTCCAACTACCACAAGTTTATA | 2 |
| G12S-FAM | TATAAACTTGTGGTAGTTGGAGCT | aGTGGC | GTAGGCAAGAGTGCCTTGACGATA | 3 |
| G12S-Ale | TATCGTCAAGGCACTCTTGCCTAC | GCCACt | AGCTCCAACTACCACAAGTTTATA | 4 |
| G12R-FAM | TATAAACTTGTGGTAGTTGGAGCT | cGTGGC | GTAGGCAAGAGTGCCTTGACGATA | 5 |
| G12R-Ale | TATCGTCAAGGCACTCTTGCCTAC | GCCACg | AGCTCCAACTACCACAAGTTTATA | 6 |
| G12C-FAM | TATAAACTTGTGGTAGTTGGAGCT | tGTGGC | GTAGGCAAGAGTGCCTTGACGATA | 7 |
| G12C-Ale | TATCGTCAAGGCACTCTTGCCTAC | GCCACa | AGCTCCAACTACCACAAGTTTATA | 8 |
| G12D-FAM | TATAAACTTGTGGTAGTTGGAGCT | GaTGGC | GTAGGCAAGAGTGCCTTGACGATA | 9 |
| G12D-Ale | TATCGTCAAGGCACTCTTGCCTAC | GCCAtC | AGCTCCAACTACCACAAGTTTATA | 10 |
| G12A-FAM | TATAAACTTGTGGTAGTTGGAGCT | GcTGGC | GTAGGCAAGAGTGCCTTGACGATA | 11 |
| G12A-Ale | TATCGTCAAGGCACTCTTGCCTAC | GCCAgC | AGCTCCAACTACCACAAGTTTATA | 12 |
| G12V-FAM | TATAAACTTGTGGTAGTTGGAGCT | GtTGGC | GTAGGCAAGAGTGCCTTGACGATA | 13 |
| G12V-Ale | TATCGTCAAGGCACTCTTGCCTAC | GCCAaC | AGCTCCAACTACCACAAGTTTATA | 14 |
| G13D-FAM | TATAAACTTGTGGTAGTTGGAGCT | GGTGaC | GTAGGCAAGAGTGCCTTGACGATA | 15 |
| G13D-Ale | TATCGTCAAGGCACTCTTGCCTAC | GtCACC | AGCTCCAACTACCACAAGTTTATA | 16 |

In addition, other non-labeled oligonucleotides such as primers were also prepared in accordance with usual oligonucleotide chemical synthesis method. The PCR reaction was carried out using the T-gradient thermoblock (a product of Biometra) and the PCR-PHFA was carried out using the ABI-7900 system (a product of ABI).

Example 1

The PCR reaction solution yielded from PCR without using a template was directly subjected to a competitive strand displacement reaction, by which the influence of the components brought by the PCR reaction solution on the strand displacement reaction was examined.

The composition of the PCR reaction solution consisted of 250 nM KF primer, 250 nM KR primer, 250 µM dNTPs, 1×PCR buffer, and 2.5 units of Taq DNA polymerase (Takara Taq Hot Start Version), with the final volume of the entire reaction solution of 100.5 µL. This PCR reaction solution was subjected to a heat treatment starting with 95° C. for 3 minutes, and then running 40 cycles, each cycle consisting of denaturation at 95° C. (20 seconds), annealing at 57° C. (30 seconds), and extension at 72° C. (30 seconds). The nucleotide sequences of the adopted KF primer and KR primer are shown in Table 2. The number in the right column shows the sequence number corresponding to the Sequence Listing.

TABLE 2

| | Nucleotide sequence | |
|---|---|---|
| KF primer | TATAAACTTGTGGTAGTTGGAGCT | 17 |
| KR primer | TATCGTCAAGGCACTCTTGCC | 18 |

The resulting PCR reaction solution (15 µL), 500 nM G12D-FAM (1 µL), 500 nM G12D-Alexa (1 µL), 2M NaCl (1 µL), and H$_2$O (2 µL) were mixed to prepare a PCR-PHFA reaction solution (denoted by "Labeled reference DNA+ PCR template (−)"). Moreover, as a control not containing the PCR reaction solution, 500 nM G12D-FAM (1 µL), 500 nM G12D-Alexa (1 µL), 2M NaCl (1 µL), 10×PCR buffer (2 µL: 100 mM Tris-HCl (pH 8.3), 500 mM KCl, and 15 mM MgCl$_2$), and H$_2$O (15 µL) were mixed (denoted by "Labeled reference DNA alone").

Using the ABI-7900 system, the changes in the fluorescence (fluorescence intensity fluctuations) in association with the temperature change of these PCR-PHFA reaction solutions were measured. The temperature condition was such that denaturation was done at 95° C. for 5 minutes, then the temperature was dropped slowly between 85° C. and 60° C. by keeping each temperature for 5 minutes per 1° C. reduction, and the temperature was finally dropped down to 35° C.

Figure 4:
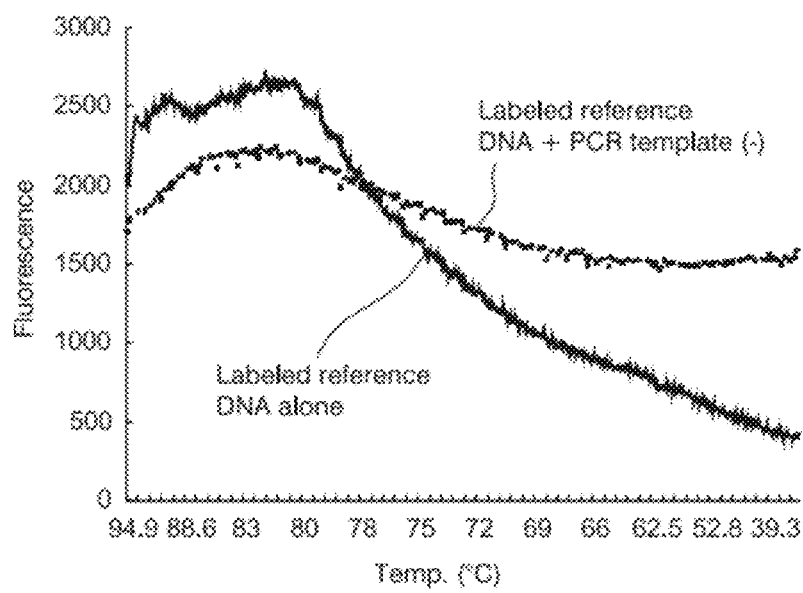
FIG. 4 is a graph showing changes in the FAM fluorescence in association with the temperature change in Example 1.

The changes in the FAM fluorescence in association with the temperature change are shown in FIG. 4. The reference DNA having the G12D genotype consisting of G12D-FAM and G12D-Alexa showed an approximately maximum fluorescence emission by having these two strands dissociated through heat denaturation (90° C.), and thereafter showed a minimum fluorescence emission as a result of the duplex formation into the initial state by the gradual lowering of the temperature (denoted by "Labeled reference DNA alone" in FIG. 4). However, when the fluorescence change was measured in the same manner by using a reaction solution upon the completion of PCR in which all the reagents but for the template had been added to this labeled reference DNA (denoted by "Labeled reference DNA+PCR template (−)" in FIG. 4), the change in the fluorescence between the single-stranded state and the double-stranded state was smaller as compared to the case where these reagents were not added (denoted by "Labeled reference DNA alone"). In other words, the change in the fluorescence in association with the temperature change from high to low temperature as seen in the labeled reference DNA alone was reduced by adding the PCR reaction solution, confirming that the proportion of the denatured labeled reference DNA reverting to the initial state was lowered by the components of the PCR reaction solution. The reason can be attributed to the phenomenon such that: the primers contained in the PCR reaction solution bound to the labeled reference DNA and thus caused an extension reaction to newly generate a non-labeled DNA strand, and this non-labeled DNA and the labeled DNA formed a duplex in the course of the gradual lowering of the temperature of the mixture of the labeled reference DNA and the PCR reaction solution without the template.

Example 2

In order to examine the influence of the PCR reaction solution on the PCR-PHFA in more detail, a PCR reaction solution without the addition of the template nor the Taq DNA polymerase and a PCR reaction solution without the addition of the template nor the primers were prepared by using the same primers and the labeled DNA as those of Example 1, and subjected to measurement of the fluorescence change in association with the temperature change in the same manner as that of Example 1.

The composition of the PCR reaction solution without the addition of the template nor the Taq DNA polymerase consisted of 250 nM KF primer, 250 nM KR primer, 250 µM dNTPs, and 1×PCR buffer, with the final volume of the entire reaction solution of 100.5 µL, (denoted by "Labeled reference DNA+PCR template (−), Taq (−)"). The composition of the PCR reaction solution without the addition of the template nor the primers consisted of 250 µM dNTPs, 1×PCR buffer, and 2.5 units of Taq DNA polymerase (Takara Taq Hot Start Version), with the final volume of the entire reaction solution of 100.5 µL, (denoted by "Labeled reference DNA+PCR template (−), Primer (−)"). These PCR reaction solutions were subjected to a heat treatment starting with 95° C. for 3 minutes, and then running 40 cycles, each cycle consisting of denaturation at 95° C. (20 seconds), annealing at 57° C. (30 seconds), and extension at 72° C. (30 seconds). The resulting PCR reaction solutions were used to prepare PCR-PHFA reaction solutions, and the fluorescence changes in association with the temperature change thereof were measured in the same manner as that of Example 1.

Figure 5:
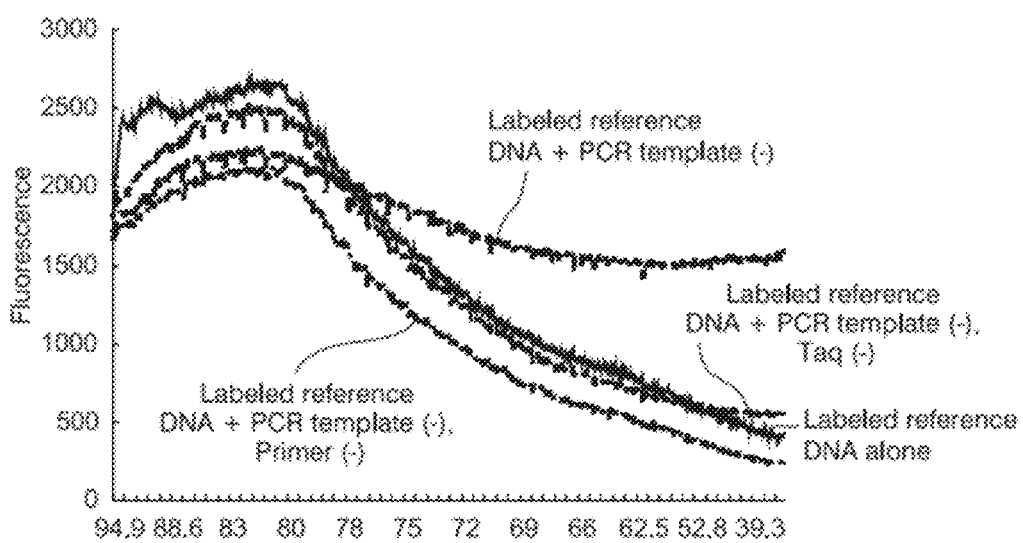
FIG. 5 is a graph showing changes in the FAM fluorescence in association with the temperature change in Example 2.

The changes in the FAM fluorescence in association with the temperature change are shown in FIG. 5. As a result, in both cases where the Taq DNA polymerase was not added (denoted by "Labeled reference DNA+PCR template (−), Taq (−)") and where the primers were not added (denoted by "Labeled reference DNA+PCR template (−), Primer (−)"), the fluorescence values at low temperatures were smaller than the case where these components were added (denoted by "Labeled reference DNA+PCR template (−)"), showing similar behavior to the case where nothing was added (denoted by "Labeled reference DNA alone").

TABLE 3

| PCR reaction solution | ΔF |
|---|---|
| Labeled reference DNA + PCR template (—) | 270 |
| Labeled reference DNA + PCR template (—), Taq (—) | 1400 |
| Labeled reference DNA + PCR template (—), primer (—) | 1495 |
| Labeled reference DNA alone | 1901 |

In order to compensate the deviation across the respective fluorescence measurements, the amounts of change ΔF in the fluorescence intensity caused by lowering the temperature of respective reactions were obtained. Specifically speaking, the ΔF value was obtained by subtracting the fluorescent value at 35° C. from the fluorescent value at 95° C., based on the Equation (1). The obtained values are shown in Table 3. This result also showed that the fluorescence change between high and low temperatures was obviously small in the case of using the PCR reaction solution without the template.

Example 3

The PCR reaction solution to be added was subjected to a heat treatment to deactivate the Taq polymerase so as inhibit the extension reaction of nucleic acids in the competitive strand displacement reaction.

First, a PCR reaction solution having the same composition as that of Example 1 was subjected to the PCR reaction under the same conditions. A part of the resulting PCR reaction solution was heated at 99° C. for 15 minutes, and the other part was heated at 99° C. for 60 minutes. These heat-treated reaction solutions and non-heated solutions were respectively used to prepare PCR-PHFA reaction solutions by using the same labeled reference DNA in the same manner as that of Example 1, and the fluorescence changes in association with the temperature change thereof were measured under the same temperature condition as that of Example 1. Moreover, the same PCR-PHFA reaction solution (denoted by "Labeled reference DNA alone") was prepared as a control not containing the PCR reaction solution, and the fluorescence change thereof was measured in the same manner as that of Example 1.

Figure 6:
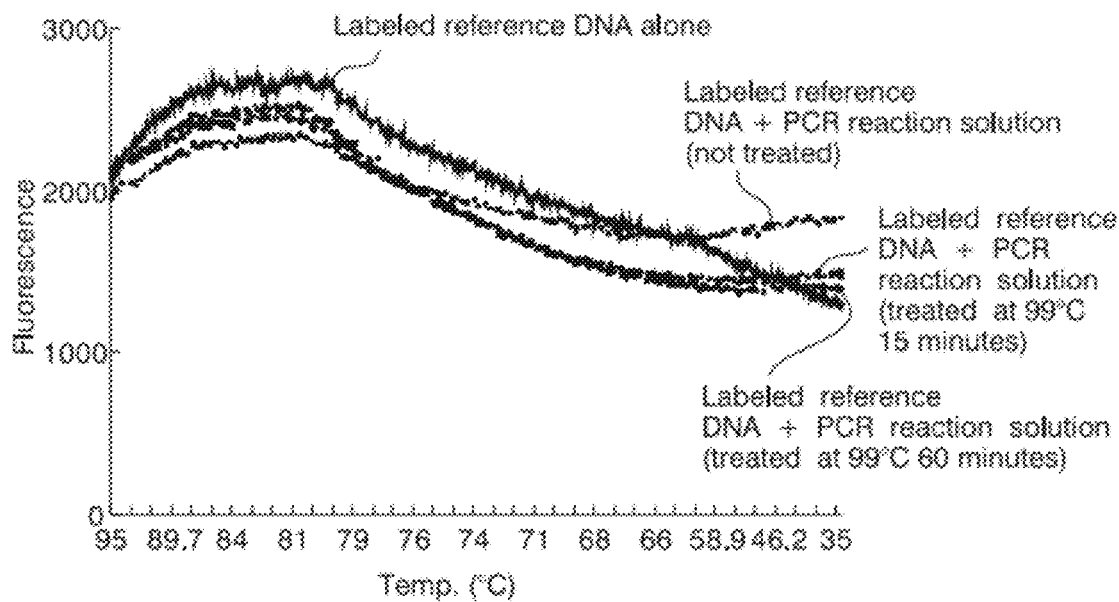
FIG. 6 is a graph showing changes in the FAM fluorescence in association with the temperature change in Example 3.

The changes in the FAM fluorescence in association with the temperature change are shown in FIG. 6. As a result, in both cases where the PCR reaction solution was heated at 99° C. for 15 minutes (denoted by "Labeled reference DNA+PCR reaction solution (treated at 99° C. 15 minutes)") and where the PCR reaction solution was heated at 99° C. for 60 minutes (denoted by "Labeled reference DNA+PCR reaction solution (treated at 99° C. 60 minutes)"), the fluorescence change between high and low temperature was smaller than the case where the PCR reaction solution was not heated (denoted by "Labeled reference DNA+PCR reaction solution (not treated)"), showing similar behavior to the case where nothing was added (denoted by "Labeled reference DNA alone").

Figure 7:
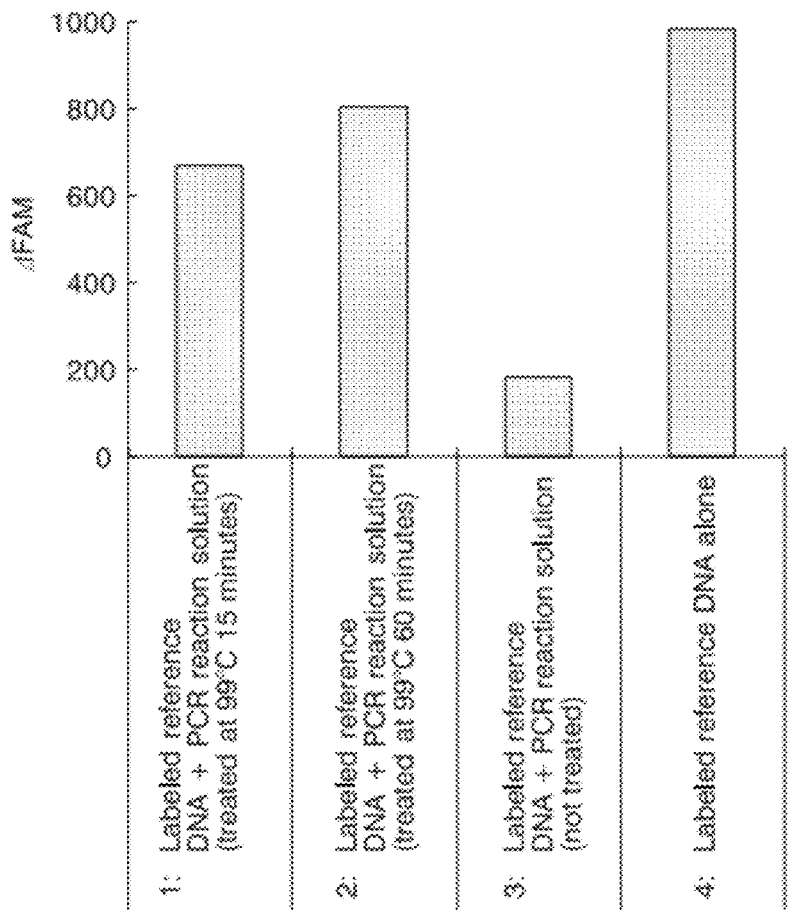
FIG. 7 is a graph showing amounts of change ΔF in the fluorescence intensity caused by lowering the temperature of respective reactions in Example 3.

Moreover, as with Example 2, the ΔF values of respective reactions were obtained by subtracting the fluorescent value at 35° C. from the fluorescent value at 95° C. FIG. 7 shows the ΔF values of respective reactions. In both cases where the PCR reaction solution was heated at 99° C. for 15 minutes and where the PCR reaction solution was heated at 99° C. for 60 minutes, the ΔF values were greater than the case where the PCR reaction solution was left unheated and directly reacted with the labeled reference DNA, and these ΔF values were closer to the case where the PCR reaction solution was not added (denoted by "Labeled reference DNA alone"). From these results, it was shown that the extension reaction in the competitive strand displacement reaction was suppressed because the activation of the Taq polymerase was lost or lowered by heating.

Example 4

EDTA was added to the PCR-PHFA reaction solution so as inhibit the extension reaction of nucleic acids in the competitive strand displacement reaction.

First, a PCR reaction solution having the same composition as that of Example 1 was subjected to the PCR reaction under the same conditions.

The resulting PCR reaction solution (15 µL), 500 nM G12D-FAM (1 µL), 500 nM G12D-Alexa (1 µL), 2M NaCl (1 µL), and H$_2$O (2 µL) were mixed to prepare a PCR-PHFA reaction solution without EDTA (denoted by "Labeled reference DNA+PCR template (−)"). Moreover, the PCR reaction solution (15 µL), 500 nM G12D-FAM (1 µL), 500 nM G12D-Alexa (1 µL), 2M NaCl (1 µL), 500 mM EDTA (0.6 µL), and H$_2$O (1.4 µL) were mixed to prepare a PCR-PHFA reaction solution with 15 mM EDTA (15 mM EDTA-containing labeled reference DNA+PCR template (−)). In the same manner, the PCR reaction solution (15 µL), 500 nM G12D-FAM (1 µL), 500 nM G12D-Alexa (1 µL), 2M NaCl (1 µL), and 500 mM EDTA (2 µL) were mixed to prepare a PCR-PHFA reaction solution with 50 mM EDTA (50 mM EDTA-containing labeled reference DNA+PCR template (−)). As a control not containing the PCR reaction solution, 500 nM G12D-FAM (1 µL), 500 nM G12D-Alexa (1 µL), 2M NaCl (1 µL), 10×PCR buffer (2 µL: 100 mM Tris-HCl (pH 8.3), 500 mM KCl, and 15 mM MgCl$_2$), and H$_2$O (15 µL) were mixed (denoted by "Labeled reference DNA alone"). The fluorescence changes in association with the temperature change of these PCR-PHFA reaction solutions were measured under the same temperature condition as that of Example 1.

Figure 8:
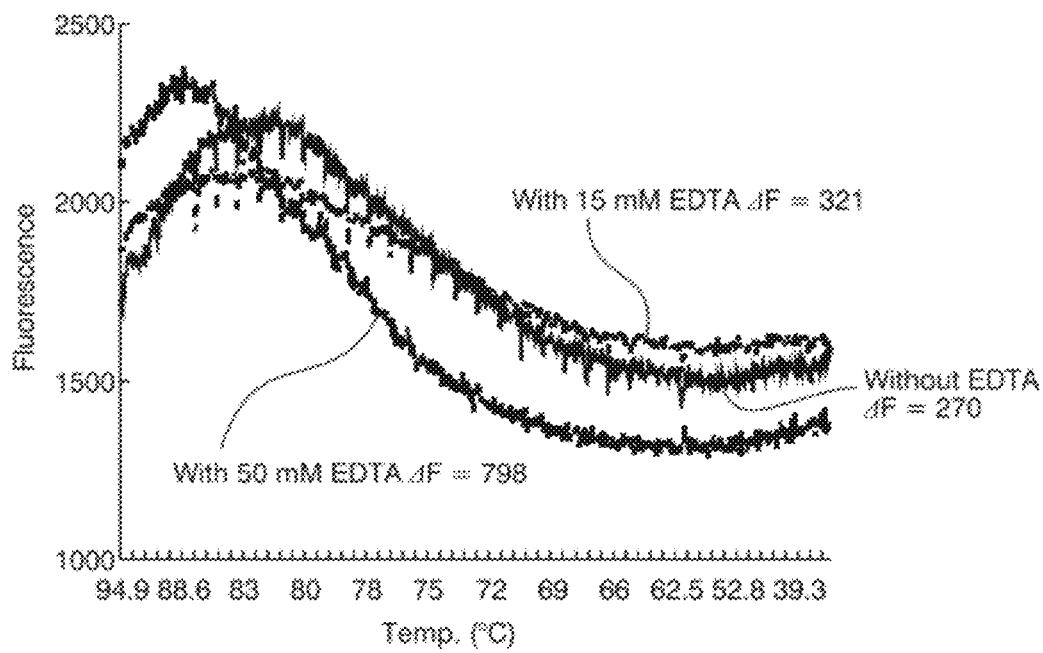
FIG. 8 is a graph showing amounts of change ΔF in the fluorescence intensity caused by lowering the temperature of respective reactions in Example 4.

The changes in the FAM fluorescence in association with the temperature change are shown in FIG. 8. As a result, in both cases where the 15 mM EDTA was added and where the 50 mM EDTA was added, the fluorescence changes between high and low temperatures were smaller than the case where EDTA was not added, showing similar behavior to the case of the labeled reference DNA alone.

Moreover, as with Example 2, the ΔF values of respective reactions were obtained by subtracting the fluorescent value at 35° C. from the fluorescent value at 95° C., which are shown in FIG. 8. It was revealed that the ΔF values were increased by the EDTA addition, as compared to the case where EDTA was not added, and these ΔF values were closer to the case of the labeled reference DNA alone.

As a result, with the EDTA concentration of 15 mM, the ΔF value was shown to be almost the same as the case without the EDTA addition, meaning that almost no improving effect was exhibited. However, with the EDTA concentration of 50 mM, the ΔF value was greater, meaning that the mismatch discrimination capability caused by the EDTA addition was drastically improved. This Example suggests that the activity of the Taq polymerase was suppressed in an EDTA addition concentration dependent manner.

In the improved PCR-PHFA method described in Patent Document 2, the PCR-PHFA reaction solution contains 1 mM EDTA. However, in Example 4, it was almost impossible for 15 mM EDTA to suppress the activity of the Taq polymerase. Therefore, it is obvious from the results of Example 4 that the conventional EDTA concentration of about 1 mM would be not effective at all to suppress the activity of the DNA polymerase, and the mismatch discrimination capability of PHFA would be lowered. In Patent Document 2, the EDTA addition is nothing more than the purpose of protecting DNA from the nuclease.

Example 5

A variety of concentrations of EDTA were added to the reaction solution of the PCR-PHFA method to examine the effect on the accuracy to discriminate genotypes.

As a specimen containing a gene whose genotype is to be distinguished, a genomic DNA extracted from cultured carcinoma-derived SW403 cells was used. Note that SW403 means cells that have been known to show a homogeneous genotype in which the second position of the K-ras gene codon 12 was mutated from guanine to thymine (G12V).

Moreover, the wild-type, G12C, G12D, G12S, and G12A genotypes were respectively used as the labeled reference DNA.

First, the SW403 genomic gene was amplified with use of the primers shown in Example 1 under the same condition as that of Example 1, thereby producing a PCR reaction solution.

Next, the labeled reference DNA of each genotype and the PCR reaction solution were mixed with EDTA at a variety of concentrations to prepare PCR-PHFA reaction solutions. Specifically speaking, when using the wild-type labeled reference DNA, 500 nM Wild-FAM (1 µL) and 500 nM Wild-Alexa (1 µL) were firstly added in a tube and solidified by drying. Then, the PCR reaction solution (14 µL), 2M NaCl (1 µL), 500 mM EDTA (X µL), and H$_2$O (5-X µL) were added thereto to prepare a PCR-PHFA reaction solution. In the case of no EDTA addition, X=0 and 5 µL, of H$_2$O were added. Moreover, 1, 2, 3, or 4 µL, (X=1, 2, 3, or 4) of 500 mM EDTA was respectively added to prepare 25 mM EDTA-containing, 50 mM EDTA-containing, 75 mM EDTA-containing, or 100 mM EDTA-containing PCR-PHFA reaction solution. The PCR-PHFA reaction solutions were also prepared in the same manner for the other genotypes.

Figure 9:
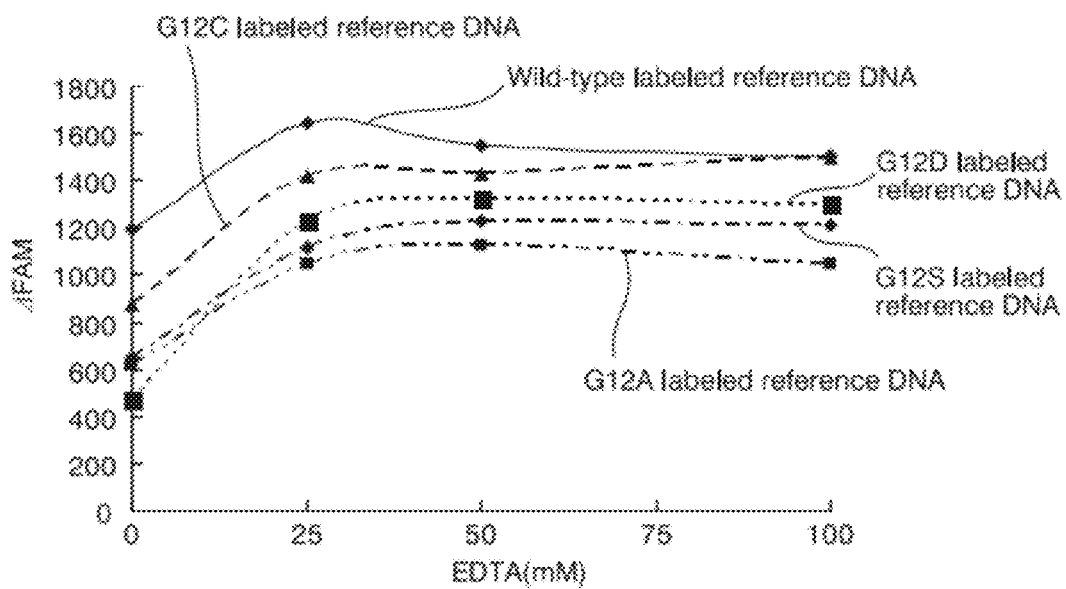
FIG. 9 is a graph showing plots of ΔF values resulting from respective reactions in Example 5, relative to the EDTA concentration.

Furthermore, the competitive strand displacement reaction was performed under the same temperature condition as that of Example 1, and the fluorescence changes in association with the temperature change of these PCR-PHFA reaction solutions were measured. Moreover, as with Example 2, the ΔF values of respective reactions were obtained by subtracting the fluorescent value at 35° C. from the fluorescent value at 95° C. FIG. 9 is a graph showing plots of ΔF values resulting from the respective reactions relative to the EDTA concentration. Since the sample (SW403) has a different genotype from any one of the added labeled reference DNAs, a greater ΔF value means better ability to clearly distinguish genotypes. Maximum ΔF values were seen when the EDTA concentration was 25 mM or higher in every combination of the sample and the labeled reference DNA, showing that 25 mM or higher EDTA concentrations were optimum for PCR-PHFA.

Example 6

The deviation was compensated by using the Index value (%) represented by the above-mentioned Equation (4) in the method for distinguishing genotypes of the present invention.

As a specimen containing a gene whose genotype is to be distinguished, a genomic DNA extracted from cultured cells that were known to have the wild type K-ras gene was used. Moreover, the wild-type, G12A, G12C, G12D, G12R, G12V, G12S, and G13D genotypes were respectively used as the labeled reference DNA.

First, the wild-type gene was amplified with use of the genomic DNA extracted from the cultured cells as a template and the primers shown in Example 1 under the same condition as that of Example 1, thereby producing a PCR reaction solution.

Next, as with Example 5, a 25 mM EDTA-containing PCR-PHFA reaction solution mixed with the labeled reference DNA of each genotype and the PCR reaction solution was prepared.

Moreover, per each genotype, a 25 mM EDTA-containing control reaction solution was prepared by adding water instead of the PCR reaction solution.

Furthermore, respectively for these 25 mM EDTA-containing PCR-PHFA reaction solution and 25 mM EDTA-containing control reaction solution, the competitive strand displacement reaction was performed under the same temperature conditions as those of Example 1, and the fluorescence changes in association with the temperature change thereof were measured.

Figure 10A:
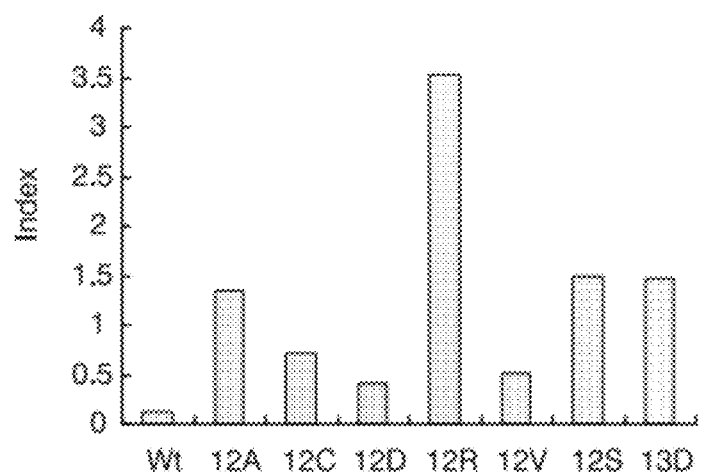
FIG. 10A is a graph showing Index values obtained from Example 6 per each genotype of labeled reference DNA, wherein the Index values have been obtained on the basis of the ratio between the fluorescent value of the acceptor labeling substance and the fluorescent value of the donor labeling substance at 35° C.

First, according to the conventional method, the ratio of the fluorescent value of the acceptor labeling substance to the fluorescent value of the donor labeling substance ([fluorescent value of the acceptor labeling substance]/[fluorescent value of the donor labeling substance]) at 35° C. upon the completion of the strand displacement reaction was obtained for use as the Index value. FIG. 10A is a graph showing the thus obtained Index values. In the graph, the symbol "Wt" represents the result of the wild-type labeled reference DNA, the symbol "12A" represents the result of the G12A labeled reference DNA, the symbol "12C" represents the result of the G12C labeled reference DNA, the symbol "12D" represents the result of the G12D labeled reference DNA, the symbol "12R" represents the result of the G12R labeled reference DNA, the symbol "12V" represents the result of the G12V labeled reference DNA, the symbol "12S" represents the result of the G12S labeled reference DNA, and the symbol "13D" represents the result of the G13D labeled reference DNA. As the specimen was wild-type, it had been expected that only the wild-type labeled reference DNA would show a low Index value while the other mutant labeled reference DNAs would not show low Index values. However, the G12V and G12D labeled reference DNAs also showed low Index values, whose differences from the Index value of the Match wild-type were small.

Figure 10B:
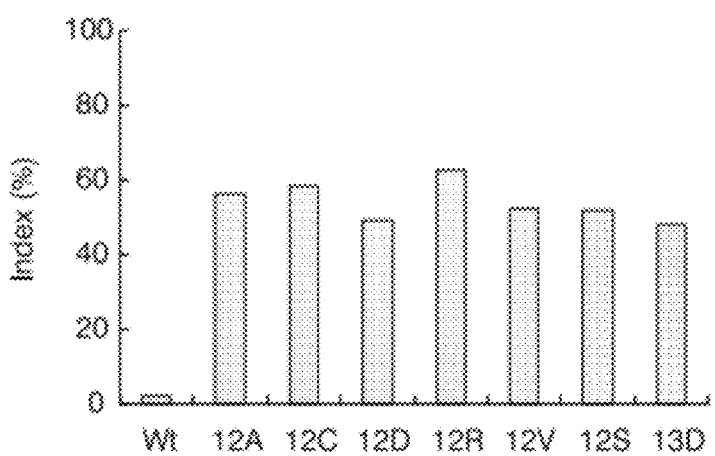
FIG. 10B is a graph showing Index values obtained from Example 6 per each genotype of labeled reference DNA, wherein the Index values have been obtained on the basis of an Equation (4) that will be described later.

On the other hand, as with Example 2, the ΔF values of the respective reactions were obtained by subtracting the fluorescent value at 35° C. from the fluorescent value at 95° C., and the Index values (%) thereof were obtained in accordance with Equation (4). FIG. 10B is a graph showing the thus obtained Index values in accordance with the Equation (4). In the graph, the symbols "Wt", "12D", and the like represent the same meanings as those of FIG. 10A. In the results, the Match wild-type labeled reference DNA showed a low Index value while all the other mutant labeled reference DNAs showed high Index values, meaning that it is obviously possible to determine that the specimen is wild-type more clearly than the conventional method as well as being possible to remarkably improve the deviation.

INDUSTRIAL APPLICABILITY

The method for distinguishing genotypes of the present invention is so excellent in the accuracy to discriminate genotypes, that applications are possible to the fields of clinical tests, in particular, to the fields of tests for somatic mutations.

The invention claimed is:

1. A method of distinguishing genotypes of a gene mutation comprising:

obtaining an amplification reaction solution which comprises a specimen double-stranded nucleic acid by amplifying a mutation site-including region of a gene contained in a specimen by a nucleic acid amplification reaction;

performing a competitive strand displacement reaction by mixing the amplification reaction solution and a reference double-stranded nucleic acid having a specific genotype on the mutation site as well as being labeled with a labeling substance to obtain a reaction solution of the competitive strand displacement reaction and then gradually lowering the temperature of the reaction solution of the competitive strand displacement reaction under a condition to suppress a polymerase extension reaction in which a concentration of EDTA as the extension reaction inhibitor is 25 mM to 50 mM in the reaction solution of the competitive strand displacement reaction, wherein out of the two nucleic acid strands constituting the reference double-stranded nucleic acid, a 3' terminal site of one strand is labeled with a first labeling substance and a 5' terminal site of another strand is labeled with a second labeling substance, and at least one of the first labeling substance and the second labeling substance is a fluorescent substance; and assessing a level of an occurrence of strand displacement between the reference double-stranded nucleic acid and the specimen double-stranded nucleic acid by using a ratio of an amount of change in a fluorescence intensity caused by the lowering the temperature of the reaction solution, to an amount of change in a fluorescence intensity caused by lowering the temperature of a control reaction solution which contains the reference double-stranded nucleic acid instead of the specimen double-stranded nucleic acid.

2. The method according to claim 1, wherein the lowering the temperature of the reaction solution is from a first temperature, which is at least a denaturation temperature at which the reference double-stranded nucleic acid and the specimen double-stranded nucleic acid denature, to a second temperature, and the amount of change in the fluorescence intensity caused by the lowering the temperature of the reaction solution is a difference between a fluorescence intensity at the first temperature and a fluorescence intensity at the second temperature.

3. The method according to claim 2, wherein the first temperature is in a range of 90 to 100° C.

* * * * *

SEQUENCE LISTING

<160> NUMBER OF SEQ ID NOS: 18

<210> SEQ ID NO 1
<211> LENGTH: 54
<212> TYPE: DNA
<213> ORGANISM: Homo sapiens

<400> SEQUENCE: 1
tataaacttg tggtagttgg agctggtggc gtaggcaaga gtgccttgac gata    54

<210> SEQ ID NO 2
<211> LENGTH: 54
<212> TYPE: DNA
<213> ORGANISM: Homo sapiens

<400> SEQUENCE: 2
tatcgtcaag gcactcttgc ctacgccacc agctccaact accacaagtt tata    54

<210> SEQ ID NO 3
<211> LENGTH: 54
<212> TYPE: DNA
<213> ORGANISM: Homo sapiens

<400> SEQUENCE: 3
tataaacttg tggtagttgg agctagtggc gtaggcaaga gtgccttgac gata    54

<210> SEQ ID NO 4
<211> LENGTH: 54
<212> TYPE: DNA
<213> ORGANISM: Homo sapiens

<400> SEQUENCE: 4
tatcgtcaag gcactcttgc ctacgccact agctccaact accacaagtt tata    54

<210> SEQ ID NO 5
<211> LENGTH: 54
<212> TYPE: DNA
<213> ORGANISM: Homo sapiens

<400> SEQUENCE: 5
tataaacttg tggtagttgg agctcgtggc gtaggcaaga gtgccttgac gata    54

<210> SEQ ID NO 6
<211> LENGTH: 54
<212> TYPE: DNA
<213> ORGANISM: Homo sapiens

<400> SEQUENCE: 6
tatcgtcaag gcactcttgc ctacgccacg agctccaact accacaagtt tata    54

<210> SEQ ID NO 7
<211> LENGTH: 54
<212> TYPE: DNA
<213> ORGANISM: Homo sapiens

<400> SEQUENCE: 7
tataaacttg tggtagttgg agcttgtggc gtaggcaaga gtgccttgac gata    54

<210> SEQ ID NO 8
<211> LENGTH: 54
<212> TYPE: DNA
<213> ORGANISM: Homo sapiens

<400> SEQUENCE: 8
tatcgtcaag gcactcttgc ctacgccaca agctccaact accacaagtt tata    54

<210> SEQ ID NO 9
<211> LENGTH: 54
<212> TYPE: DNA
<213> ORGANISM: Homo sapiens

<400> SEQUENCE: 9
tataaacttg tggtagttgg agctgatggc gtaggcaaga gtgccttgac gata        54

<210> SEQ ID NO 10
<211> LENGTH: 54
<212> TYPE: DNA
<213> ORGANISM: Homo sapiens

<400> SEQUENCE: 10
tatcgtcaag gcactcttgc ctacgccatc agctccaact accacaagtt tata        54

<210> SEQ ID NO 11
<211> LENGTH: 54
<212> TYPE: DNA
<213> ORGANISM: Homo sapiens

<400> SEQUENCE: 11
tataaacttg tggtagttgg agctgctggc gtaggcaaga gtgccttgac gata        54

<210> SEQ ID NO 12
<211> LENGTH: 54
<212> TYPE: DNA
<213> ORGANISM: Homo sapiens

<400> SEQUENCE: 12
tatcgtcaag gcactcttgc ctacgccagc agctccaact accacaagtt tata        54

<210> SEQ ID NO 13
<211> LENGTH: 54
<212> TYPE: DNA
<213> ORGANISM: Homo sapiens

<400> SEQUENCE: 13
tataaacttg tggtagttgg agctgttggc gtaggcaaga gtgccttgac gata        54

<210> SEQ ID NO 14
<211> LENGTH: 54
<212> TYPE: DNA
<213> ORGANISM: Homo sapiens

<400> SEQUENCE: 14
tatcgtcaag gcactcttgc ctacgccaac agctccaact accacaagtt tata        54

<210> SEQ ID NO 15
<211> LENGTH: 54
<212> TYPE: DNA
<213> ORGANISM: Homo sapiens

<400> SEQUENCE: 15
tataaacttg tggtagttgg agctggtgac gtaggcaaga gtgccttgac gata        54

<210> SEQ ID NO 16
<211> LENGTH: 54
<212> TYPE: DNA
<213> ORGANISM: Homo sapiens

<400> SEQUENCE: 16
tatcgtcaag gcactcttgc ctacgtcacc agctccaact accacaagtt tata        54

<210> SEQ ID NO 17
<211> LENGTH: 24
<212> TYPE: DNA
<213> ORGANISM: Artificial Sequence
<220> FEATURE:

```
<223> OTHER INFORMATION: Description of Artificial Sequence: KF Primer.

<400> SEQUENCE: 17
tataaacttg tggtagttgg agct                                              24

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: KR Primer.

<400> SEQUENCE: 18
tatcgtcaag gcactcttgc c                                                 21
```